US012740804B2

(12) United States Patent
Garvey et al.

(10) Patent No.: US 12,740,804 B2

(45) **Date of Patent: *Sep. 22, 2026**

(54) MODULAR, ASSEMBLED SURGICAL INSTRUMENT

(71) Applicant: Mission Surgical Innovations, LLC, Wayne, PA (US)

(72) Inventors: Brian Garvey, Bryn Mawr, PA (US); Sidney M. Jacoby, Gladwyne, PA (US); Eon Kyu Shin, Princeton, NJ (US); Patrick Kane, Ocean City, NJ (US)

(73) Assignee: MISSION SURGICAL INNOVATIONS, LLC, Wayne, PA (US)

( * ) Notice: Subject to any disclaimer, the term of this patent is extended or adjusted under 35 U.S.C. 154(b) by 199 days.

This patent is subject to a terminal disclaimer.

(21) Appl. No.: 18/649,049

(22) Filed: Apr. 29, 2024

(65) Prior Publication Data

US 2024/0285310 A1 Aug. 29, 2024

Related U.S. Application Data

(63) Continuation of application No. 16/577,929, filed on Sep. 20, 2019, now Pat. No. 11,969,186.

(51) Int. Cl.

| | |
|---|---|
| ***A61B 17/34*** | (2006.01) |
| ***A61B 1/05*** | (2006.01) |
| ***A61B 17/32*** | (2006.01) |
| ***A61B 90/00*** | (2016.01) |

(52) U.S. Cl.

CPC ............ *A61B 17/3403* (2013.01); *A61B 1/05* (2013.01); *A61B 17/320016* (2013.01);

(Continued)

(58) Field of Classification Search

CPC ......... A61B 2017/320032; A61B 2017/32004; A61B 2017/3407; A61B 2017/00455;

(Continued)

(56) References Cited

U.S. PATENT DOCUMENTS

| | | | |
|---|---|---|---|
| 5,273,024 | A | 12/1993 | Menon et al. |
| 5,827,312 | A | 10/1998 | Brown et al. |

(Continued)

FOREIGN PATENT DOCUMENTS

| | | | |
|---|---|---|---|
| WO | 2007/145716 | A2 | 12/2007 |
| WO | 2015/033907 | A1 | 3/2015 |

*Primary Examiner* — Jocelin C Tanner

(74) *Attorney, Agent, or Firm* — Volpe Koenig

(57) ABSTRACT

A surgical device including a cannula having a base member at a proximal end, a sidewall connected to the base member, and a bore defined by the base member and sidewall. The sidewall further has an opening into the bore between axially-extending edges of the sidewall. A configurable guide insert includes a combination track having a circular opening for insertion of a camera device and a slot opening for insertion of a cutting instrument. The configurable guide insert may be permanently or detachably coupled to the base member and is positionable in a right orientation for a procedure in a patient's right side or in a left orientation for a procedure in a patient's left side. The combination track slidably receives a camera device through the circular opening into the bore and slidably receives a surgical implement through the slot opening and into an action area outside the bore.

20 Claims, 14 Drawing Sheets

(52) U.S. Cl.
CPC ...... *A61B 17/320036* (2013.01); *A61B 90/08* (2016.02); *A61B 2017/3407* (2013.01); *A61B 2090/0811* (2016.02)

(58) Field of Classification Search
CPC . A61B 2090/0811; A61B 90/94; A61B 90/08; A61B 17/3403; A61B 17/320036; A61B 17/320016; A61B 1/0014; A61B 1/05
USPC .......................................................... 606/108
See application file for complete search history.

(56) References Cited

U.S. PATENT DOCUMENTS 6,569,085 B2 5/2003 Kortenback et al.
7,431,694 B2 10/2008 Stefanchik et al.
7,780,690 B2 8/2010 Rehnke
8,257,379 B2 9/2012 Lee
8,273,098 B2 9/2012 Strickland
8,523,891 B2 9/2013 Welborn
8,523,892 B2 9/2013 Rehnke et al.
8,672,960 B2 3/2014 Briganti et al.
10,806,481 B2 * 10/2020 Bright ............ A61B 17/320016
11,969,186 B2 * 4/2024 Garvey ................ A61B 1/0014
2010/0228085 A1 9/2010 Mirza et al.
2012/0016397 A1 * 1/2012 Briganti ......... A61B 17/320036 606/167
2012/0016398 A1 1/2012 Strickland
2014/0066709 A1 3/2014 Mirza et al.
2016/0157881 A1 * 6/2016 Seymour ........ A61B 17/320036 606/172
2017/0042566 A1 2/2017 Mirza et al.
2019/0150900 A1 5/2019 Choung et al.

* cited by examiner

MODULAR, ASSEMBLED SURGICAL INSTRUMENT

CROSS REFERENCE TO RELATED APPLICATION

This application is a continuation of U.S. patent application Ser. No. 16/577,929 filed on Sep. 20, 2019, which will issue as U.S. Pat. No. 11,969,186 on Apr. 30, 2024, the contents of which are hereby incorporated by reference herein.

FIELD OF INVENTION

The present disclosure relates to a surgical device, and, more particularly, to a surgical device including a configurable guide insert that may permanently or detachably couple to a cannula, where the configurable guide insert provides for the user's selection of either a left or a right orientation of the surgical device based upon whether the surgical procedure will be performed on the left side or the right side of a patient.

BACKGROUND

Several soft tissue procedures involve the division or release of a soft tissue (ligament, tendon, muscle, fascia, etc.) with a knife blade to decompress adjacent nerves or other soft tissues. Conventional soft tissue surgery is performed either in an open manner with large incisions; in a mini-open manner with a smaller incision, or endoscopically with the assistance of visualization and tissue manipulation through one of several types of guides or apparatuses. Open procedures are more disruptive to the patient and often do not utilize surgical guides to protect the adjacent soft tissue structures. Open and mini-open procedures require the incision to be placed directly over the structure subject to release. Often times the incision in an open or mini-open procedure must be made in an anatomic location that provides additional discomfort to the patient and increased potential for post-operative complications. Endoscopic systems comprise guides that allow the incision placement adjacent to the tissue being released. Surgeons then have more variability in the placement of the incision which provides the patient with a potential for faster recovery and decreased pain or discomfort post-surgery.

Conventional endoscopic systems have several limitations depending on their independent design features. Many conventional endoscopic systems do not allow the blade and endoscope or arthroscope to move independently from each other. These systems require the scope or camera to be mounted to the cannula and blade mechanism, which may be static or deployed through a secondary mechanism. The inability to move the camera and blade independently through a guide or cannula limits the physical control and visualization available to the surgeon. The surgeon must move the entire assembly of the camera, guide and knife as one unit, and cannot reposition the camera relative to the knife or guide. This can prevent the surgeon from confirming with 100% certainty that the soft tissue was appropriately manipulated or released. Additionally, the inability to move the blade and camera independently of each other provides the potential for the surgeon to cut adjacent soft tissues, such as nerves, without knowing. Also if the view through the camera becomes obscured via moisture or debris, the surgeon must remove the entire apparatus from the body, disassemble the camera from the guide and blade, remove the obstruction to the view, reassemble and reinsert the apparatus. This practice adds significant time and inconvenience to the surgery.

Further, in the area of endoscopic systems for soft tissue release, the position of the surgical implement, such as the blade, relative to the camera of the endoscope or arthroscope, becomes significant. More particularly, when the camera of the endoscope or arthroscope is positioned below the surgical implement—in a top-to-bottom configuration—the efficiency of insertion and placement of the device at the incision point may be compromised, as it is more difficult for the physician to place a device having a top-to-bottom configuration, at a narrow incision point. In addition, when the camera is beneath the scope, the top-to-bottom relationship may also compromise the physician's ability to view the procedure via the camera device to observe the action of the surgical implements. Accordingly, there is a need for an endoscopic soft tissue release device that provides improved functionality for insertion and placement of the device and cannula, while also providing improved visibility of the surgical implements during the procedure. It would be advantageous to implement an endoscopic soft tissue release device that features one or more surgical implements in a position that is horizontally adjacent to the cannula, thereby providing improved functionality for insertion and placement of the device at narrow incision points and improved visibility of the implements during surgery.

In addition, the location of a surgical incision point becomes significant in relation to the physician's objective to operate on targeted soft tissue structures for the division or release of a soft tissue (ligament, tendon, muscle, fascia, etc.). In addition to the targeted soft tissue structures, the physician must also account for the non-targeted, adjacent soft tissue structures. Whether a surgical incision point resides on the left or right side of a particular anatomical structure, such as the hand, involves additional consideration for avoiding contact of a surgical implement, such as a cutting instrument, with the adjacent soft tissue structures of the left or right hand during a surgical procedure. For example, when an incision point resides at the ulnar side of a patient's left hand, the physician must remain away from non-targeted soft tissue structures when manipulating a cutting instrument. Accordingly, it would be advantageous if the physician were able to configure an endoscopic soft tissue release device at the time of surgery based upon where the incision will be made at a particular point of an anatomical structure, such as the ulnar side of a patient's left or right hand. The ability to position such an endoscopic soft tissue release device in the optimum orientation with respect to the location of the incision and surrounding soft tissue structures would provide for a more efficient and ergonomic surgical device.

In addition, the orientation of a camera device and a cutting instrument within a cannula that is utilized for division or release of a soft tissue, may also be considered in relation to whether the physician is left or right handed. For example, when performing a soft tissue release procedure on the ulnar side of the wrist, the ability of the physician to perform each surgical maneuver ergonomically in preference to the physician's dominant hand may also be a significant factor. Accordingly, there is a need for an improved endoscopic soft tissue release device that enables the physician to configure the surgical instrument to achieve ergonomic advantages relative to the location of the incision point and the dominant hand of the physician.

The present disclosure is directed to overcoming one or more problems of the prior art.

SUMMARY

In one aspect, the present disclosure is directed to a cannula for use as part of a surgical device. The cannula includes a base member at a proximal end, a sidewall connected to the base member and extending in an axial direction from the proximal end to a distal end, a bore extending in the axial direction defined by the base member and the sidewall, the sidewall further defining an opening into the bore between axially-extending edges of the sidewall, and a configurable guide insert coupled to the base member. The configurable guide insert includes a combination track including a circular opening and a slot opening. The circular opening extends through the configurable guide insert and through the base member into the bore, and the slot opening extends through the configurable guide insert and through the base member and into an action area outside of the bore and radially between the edges of the sidewall. The combination track is configured to slidably receive a first surgical implement through the circular opening and into the bore and slidably receive a second surgical implement through the slot opening and into the action area. The configurable guide insert is positionable in a right orientation for positioning of the first and second surgical implements for a surgical procedure in the right side of a patient, or in a left orientation for positioning of the first and second surgical implements for the surgical procedure in the left side of the patient. The configurable guide insert is configured for rotation of 180 degrees by a user relative to an axis defined by the cannula when positioning the configurable guide insert on the base member in the right orientation or in the left orientation. Finally, the configurable guide insert includes a set of markings configured to indicate whether the configurable guide insert is coupled to the base member in the right orientation for the surgical procedure in the right side of the patient or in the left orientation for the surgical procedure in the left side of the patient.

In another aspect, the present disclosure is directed to a surgical device. The surgical device includes a configurable guide insert having a combination track including a circular opening and a slot opening, where each of the circular opening and the slot opening extends through the configurable guide insert. The configurable guide insert further includes a set of markings and may be positioned in a right orientation for a surgical procedure in a right side of a patient or in a left orientation for a surgical procedure in a left side of patient, and the markings indicate whether the configurable guide insert is positioned in the right orientation or the left orientation. The surgical device further includes a first surgical implement, a second surgical implement including an acting feature and a sliding feature, and a cannula comprising a base member at a proximal end, a sidewall connected to the base member and extending in an axial direction from the proximal end to a distal end, and a bore extending in the axial direction defined by the base member and the sidewall. The sidewall further defines an opening into the bore between axially-extending edges of the sidewall, wherein the configurable guide insert detachably couples to the base member and the circular opening extends through the base member into the bore and the slot opening extends through the base member into an action area outside of the bore and radially between the edges of the sidewall. The combination track slidably receives the first surgical implement through the circular opening and into the bore and slidably receives the second surgical implement through the slot opening and into the action area via the sliding feature. The configurable guide insert detachably couples in the right orientation for positioning of the first and second surgical implements for a surgical procedure in the right side of the patient, or in the left orientation for positioning of the first and second surgical implements for the surgical procedure in the left side of the patient. The configurable guide insert is configured for rotation of 180 degrees by a user relative to an axis defined by the cannula when detachably coupling the configurable guide insert to the base member from the right orientation to the left orientation or from the left orientation to the right orientation.

In another aspect, the present disclosure is directed to a surgical device. The surgical device includes a configurable guide insert having a combination track including a circular opening and a slot opening, where each of the circular opening and the slot opening extends through the configurable guide insert. The configurable guide insert further includes a set of markings and may be positioned in a right orientation for a surgical procedure in the right side of the patient or in a left orientation for a surgical procedure in the left side of the patient, and the markings indicate whether the configurable guide insert is positioned in the right orientation or the left orientation. The surgical device further includes an obturator and a cannula comprising a base member at a proximal end, a sidewall connected to the base member and extending in an axial direction from the proximal end to a distal end, and a bore extending in the axial direction defined by the base member and the sidewall. The sidewall further defines an opening into the bore between axially-extending edges of the sidewall, wherein the configurable guide insert detachably couples to the base member and the circular opening extends through the base member into the bore and the slot opening extends through the base member into an action area outside of the bore and radially between the edges of the sidewall. The combination track slidably receives the obturator through the circular opening and into the bore when the configurable guide insert is positioned in the right orientation for the surgical procedure in the right side of the patient or in the left orientation for the surgical procedure in the left side of the patient. The configurable guide insert is configured for rotation of 180 degrees by a user relative to an axis defined by the cannula when detachably coupling the configurable guide insert to the base member from the right orientation to the left orientation or from the left orientation to the right orientation.

In yet another aspect, the present disclosure is directed to a method of performing a surgical procedure. The method includes providing a cannula wherein the cannula includes a base member and a configurable guide insert coupled to the base member. The method further includes providing a removable obturator configured to slidably insert within the cannula through the configurable guide insert and base member. The configurable guide insert includes a marking to indicate whether the configurable guide insert is positioned in a right orientation or in a left orientation. In addition, the configurable guide insert defines a combination track, wherein the combination track includes both a circular opening extending through the configurable guide insert and into a bore within the cannula formed by the sidewall of the cannula, and a slot opening extending through the configurable guide insert and into an action area outside of the bore and radially between axially-extending edges of the sidewall. The method further includes determining whether the configurable guide insert will be positioned in the right orientation for a surgical procedure in the right side of a patient or in the left orientation for a surgical procedure in the left side of patient, wherein the configurable guide insert is configured for rotation of 180 degrees by a user relative to an axis defined by the cannula between the right orientation and the left orientation, or between the left orientation and the right orientation. The method further includes rotating the configurable guide insert within the base member in either the right orientation for the surgical procedure in the right side of the patient or in the left orientation for the surgical procedure in the left side of the patient. The method further includes inserting the obturator into the bore through the circular opening of the combination track and sliding the obturator toward a distal end of the cannula, inserting the cannula into an incision in either the left side of the patient or the right side of the patient, removing the obturator from the cannula while leaving the cannula in place within the incision in either the left side of the patient or the right side of the patient, inserting a camera device into the bore through the circular opening of the combination track and sliding the camera device toward a distal end of the cannula, providing an image of a target tissue via the camera device, inserting a tissue manipulation device through the slot opening of the combination track and sliding the tissue manipulation device toward the distal end of the cannula and into the action area, and manipulating the target tissue via the tissue manipulation device.

BRIEF DESCRIPTION OF THE DRAWINGS

The foregoing summary and the following detailed description will be better understood when read in conjunction with the appended drawings, which illustrate a preferred embodiment of the invention. In the drawings.

DETAILED DESCRIPTION OF THE PREFERRED EMBODIMENT(S)

Figure 1A:
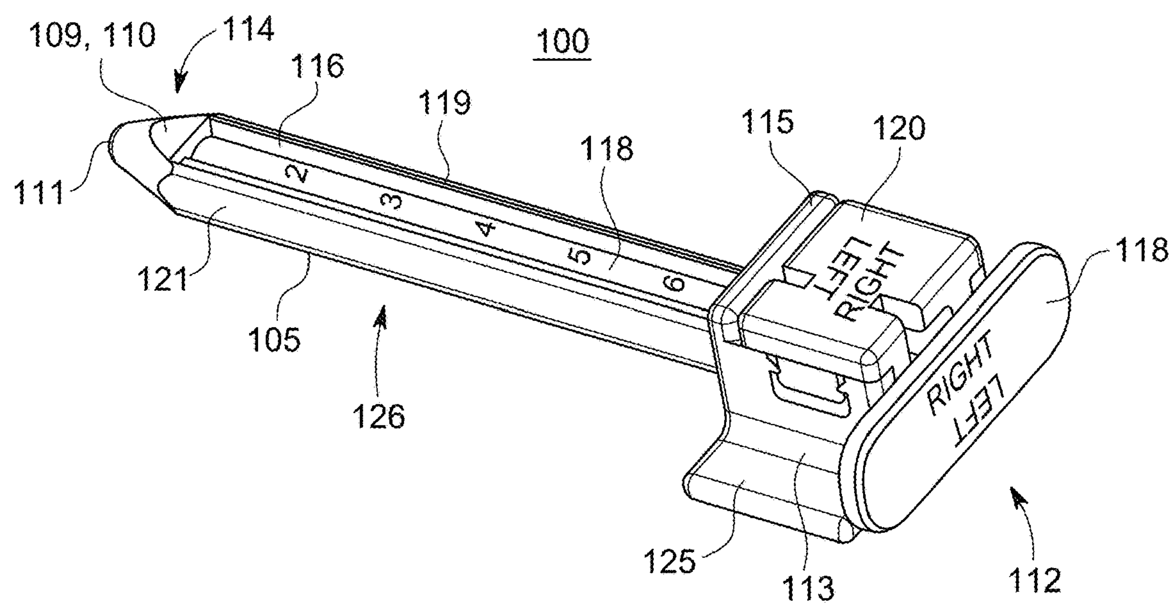
FIG. 1A is a side-perspective view of the surgical device with all components in place.

Various embodiments of the invention are described in the following paragraphs. Where like elements have been depicted in multiple embodiments, identical or similar reference numerals have been used for ease of understanding.

The present disclosure provides a surgical device which is generally applicable to procedures that include the insertion of an implement through an incision and the manipulation of a selected tissue with at least one implement. The disclosed surgical device includes multiple components, which are used in conjunction with each other to execute the surgical procedure and which include features that enhance and ease such execution.

The disclosed surgical device includes a cannula, which forms a base structure, a configurable guide insert that detachably couples to the cannula and includes a combination track defined along an axis of the cannula, and an obturator that may be inserted through the combination track of the configurable guide insert and into the cannula along the axis of the cannula. The combination track of the configurable guide insert may include one contiguous opening with space to accommodate insertion of multiple surgical instruments, where the surgical instruments are restricted to only stay within their respective designated regions within the singular contiguous opening through the combination track of the configurable guide insert. More specifically, the singular contiguous opening through the combination track of the configurable guide insert may include at least a circular opening and a slot opening, which define axially-extending spaces for receiving other components of the surgical device. The circular opening and slot opening define the designated regions within the singular contiguous opening through the combination track of the configurable guide insert for the restricted positioning and movement of the surgical instruments within the combination track of the configurable guide insert. For example, the circular opening may receive a first surgical implement and the slot opening may receive a second surgical implement. The first implement may be a camera device, which provides an internal view of a target tissue for a physician performing the procedure. The second surgical implement may be a tissue manipulation device, which is guided by the physician performing the procedure and which may be used to manipulate (e.g., cut) the target tissue. In particular, a tissue manipulation device may be any of a rasp, a forward cutting knife, a reverse cutting knife, or any other surgical implement, for example.

The disclosed cannula having a configurable guide insert with combination track provides an improved mechanism for performing a tissue manipulation procedure. In one embodiment, the circular opening and the slot opening of the combination track, which may be interconnected in space, allow the different surgical implements to be positioned in close proximity to each other, providing for effective interaction and use of the implements. The combination track of the configurable guide insert allows the surgical implements to interact with each other, such as to allow one implement to provide a guide structure for the other implement. In addition, the configurable guide insert provides enhanced functionality by enabling the physician to select between the two configurations for the device during a surgical procedure. The configurable guide insert may be detachably coupled to the base member of the cannula in a selected orientation with respect to the incision point of an anatomical structure, such as the ulnar side of a patient's left or right hand. Markings on the configurable guide insert indicate the respective orientation of the device, so that the physician may quickly assemble the device by detachably coupling the configurable guide insert to the cannula, for a rigid attachment of the cannula, configurable guide insert and obturator components, in the optimum orientation, for insertion of the device at a designated incision point in a left side or right side of a patient.

In addition to the ability to assemble the device in a desired configuration, the device also provides an additional ergonomic advantage based upon the side-to-side positioning of the first and second surgical implements within the cannula. Current endoscopic systems for soft tissue release are difficult for the physician to insert and place at the incision point because the position of the surgical implement, such as the cutting tool, is oriented below the camera device, in a top-to-bottom relationship. When the cannula features a cutting tool above the camera, the height of the cannula is greater, making it more cumbersome to insert the cannula at a narrow incision point. Moreover, the physician's visibility of the cutting tool via the camera device may be compromised when the camera is below the cutting tool. Therefore, a cannula featuring surgical implements on the lateral sides of the camera, to reduce the height of the cannula, may simplify insertion of the cannula at the narrow incision point while also improving the physician's visibility of the surgical implements via the camera device. Accordingly, in the disclosed cannula with configurable guide insert having a combination track, a camera device may be positioned directly adjacent to—and on a lateral side of—a surgical implement, providing optimum visibility for performance of the surgical procedure. The horizontally adjacent positioning of the camera relative to the lateral side of the surgical implement not only improves visibility for the physician during simultaneous use of multiple surgical implements at one time, it also provides improved ergonomic functionality for insertion and placement of the cannula at the incision point. It may be preferable and less cumbersome for the physician to insert the cannula if the surgical implements are positioned laterally adjacent to the camera, rather than in a top-to-bottom relationship, relative to the camera.

Further, the disclosed surgical device may be provided to the physician at the time of surgery in a single kit that includes the cannula, configurable guide insert and obturator. The kit may be a sterile packaged kit for surgery that may be assembled at the time of an operation with additional functionality to configure the device in the desired orientation for targeting of soft tissue in a patient's left or right side, such as a left or right hand, for example.

Figure 1B:
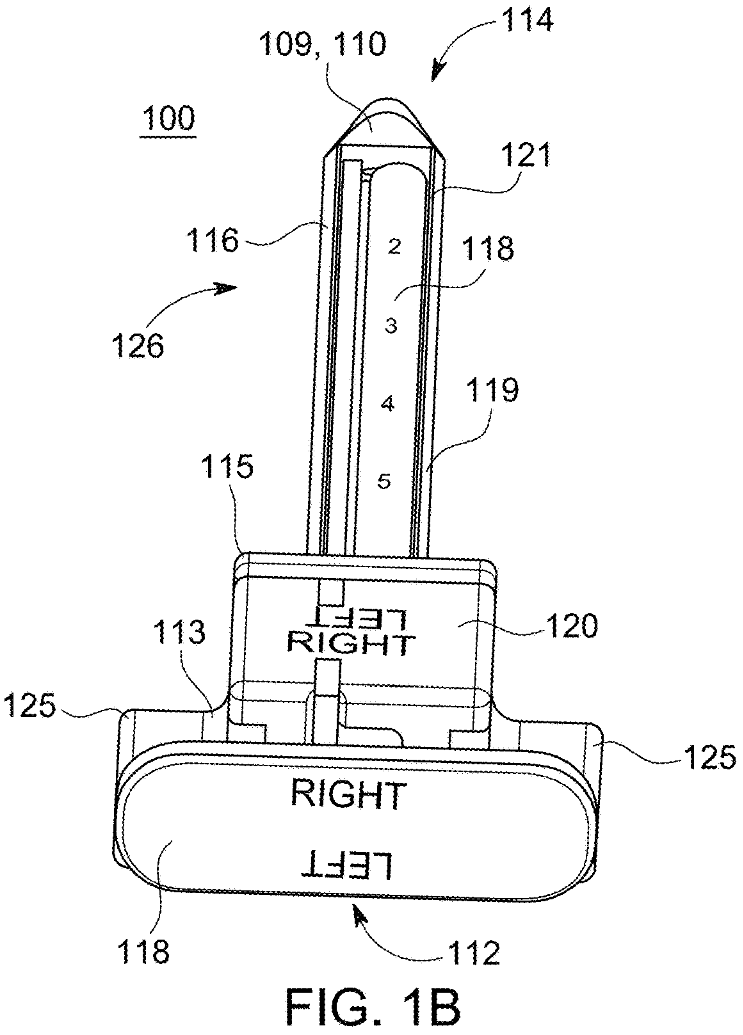
FIG. 1B is a perspective view showing the proximal end of the surgical device with all components in place.

FIGS. 1A and 1B illustrate perspective views, respectively, of an exemplary surgical device 100. The surgical device 100 is configured to be used in a surgical procedure, such as a tissue manipulation procedure. For example, the surgical device 100 may be configured to be used in a procedure for releasing, excising, or modifying soft tissue structures. Examples of such procedures, which may be carried out using the surgical device 100 include carpal tunnel release, cubital tunnel release, trigger finger release, gastrocnemius release, and plantar facia release. These and similar procedures normally include minimally-invasive techniques, which are generally assisted through the use of a device (e.g., a camera) that provides visualization of an internal structure, which is being targeted for the procedure. The surgical device 100 includes features, which allow for such a visualization device to be used in combination with an implement, used to carry out the surgical component of the procedure. The surgical device 100 provides for simultaneous use of multiple surgical implements at one time. The first surgical implement may be a camera device, such as an endoscope or an arthroscope, and the second surgical implement may be a tissue manipulation device, such as a rasp, a probe, a hook, a feeler, a reverse or antegrade cutting implement, a forward cutting implement, or the like. The first surgical implement as a camera device may include conventional components (e.g., camera components, electronic components, connector components) which allow an image to be presented to a physician performing the procedure (e.g., via a connected display). These and other objects, features and advantages of the example surgical device 100 will be described in further detail in the following illustrative embodiments thereof.

Consistent with disclosed embodiments, as seen in FIGS. 1A-1B, the surgical device 100 may include a cannula 105, having a proximal end 112 and a distal end 114 along an axial direction of the cannula 105, and a bore 116 extending along the axial direction through the cannula 105. The cannula 105 includes a base member 113 at the proximal end 112, an end portion 109 at the distal end 114, and a tubular body portion 126 formed there between. The end portion 109 may include a support surface 110. The bore 116 may extend an entire length of the cannula 105. In an embodiment, the end portion 109 is closed to act as a stop for the first surgical implement, such as a camera device.

Figure 8A:
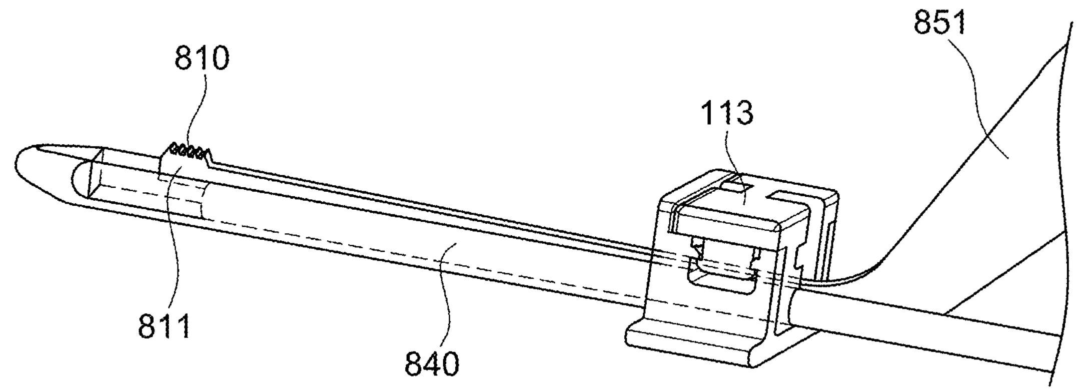
FIG. 8A is a side view of a rasp within an exemplary surgical device.
Figure 8B:
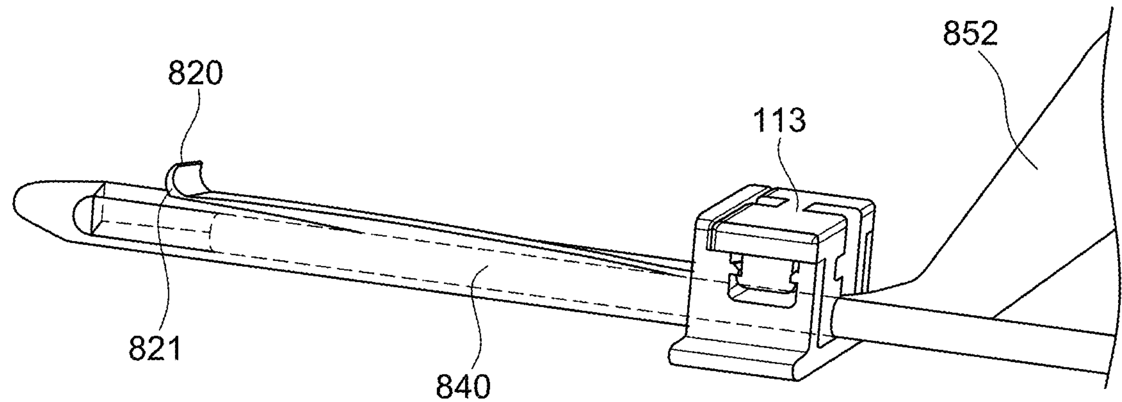
FIG. 8B is a side view of a reverse cutting knife within an exemplary surgical device.
Figure 8C:
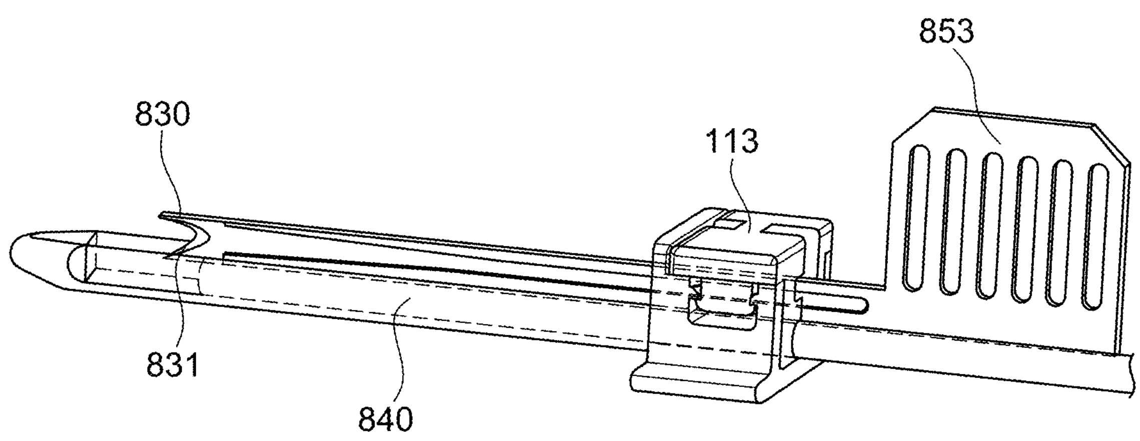
FIG. 8C is a side view of a forward cutting knife within an exemplary surgical device.

Referring again to FIGS. 1A-1B, the tubular body portion 126 forms a surface for supporting and guiding at least one surgical implement, such as a camera device, in some manner. The tubular body portion 126 extends axially from the base member 113 to the support surface 110. The tubular body portion 126 includes a sidewall 119, which extends radially to form a supporting member for at least one surgical implement, which may be the camera device or a cutting implement, for example. The sidewall 119 extends axially and radially and defines the bore 116 therethrough and includes a pair of axially-extending edges 121, which define an opening into the bore 116 (e.g., from above). In an exemplary embodiment, the area between the edges 121 of the sidewall 119 is also above the opening into the bore 116 when the cannula 105 is inserted into a patient through an incision (i.e., during use). In a particular embodiment, the area between the edges 121 is entirely above the opening into the bore 116. As seen in FIGS. 1A-1B, the sidewall 119 extends radially to form a semi-rectangular shape with an open top area between the axially-extending edges 121 of the sidewall 119. It should be understood, however, that the sidewall 119 could be formed in other shapes, including a closed circle, semi-circle, hexagonal, etc., and may include openings at radial positions other than or in addition to the top opening. In general, the tubular body portion 126 forms a surface for supporting and guiding the first surgical implement 840 (such as a camera device as shown in FIGS. 8A-8C) in some manner.

In an exemplary embodiment, the support surface 110 at the distal end 114 of the cannula 105 is an extension of the sidewall 119 such that a closed tubular portion is formed. In some embodiments, the support surface 110 is a flat surface extending in a direction perpendicular to the axial direction. In the illustrated embodiment, the support surface 110 also extends along the axially-extending edges 121 of the sidewall 119 in an axial direction. The support surface 110 also provides a stop for the surgical implements. In another embodiment, the support surface 110 may include an aperture 111 to enable a camera device to have an axial line of sight through the aperture 111. The diameter of the aperture 111 may be as large or as small as needed to accommodate an axial line of sight for the camera device, through the aperture 111.

Figure 11A:
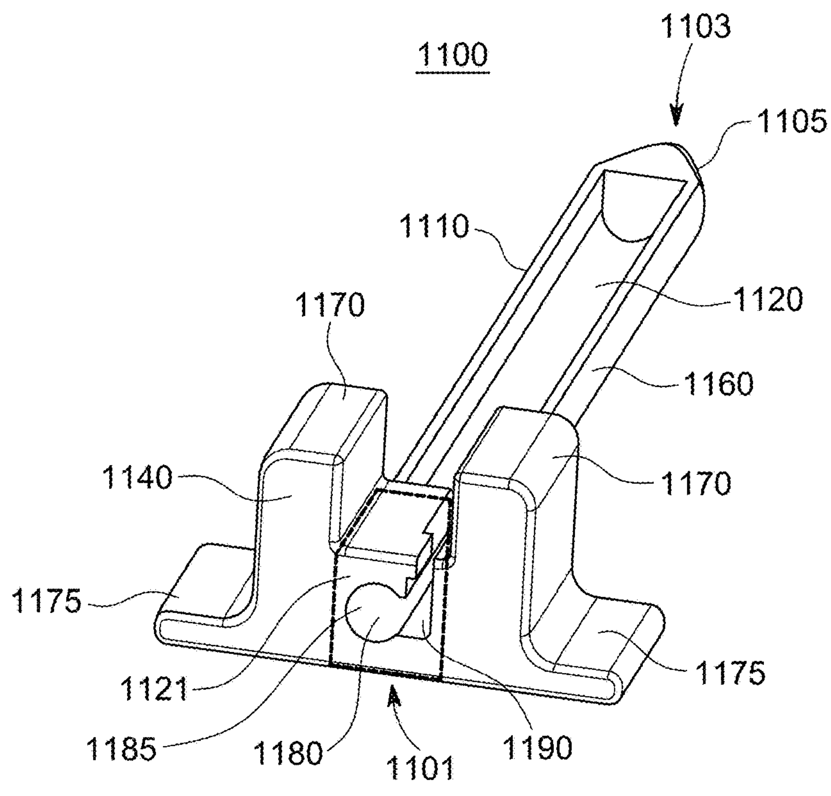
FIG. 11A is a perspective view of an additional embodiment of the surgical device showing the proximal end of the device.
Figure 11B:
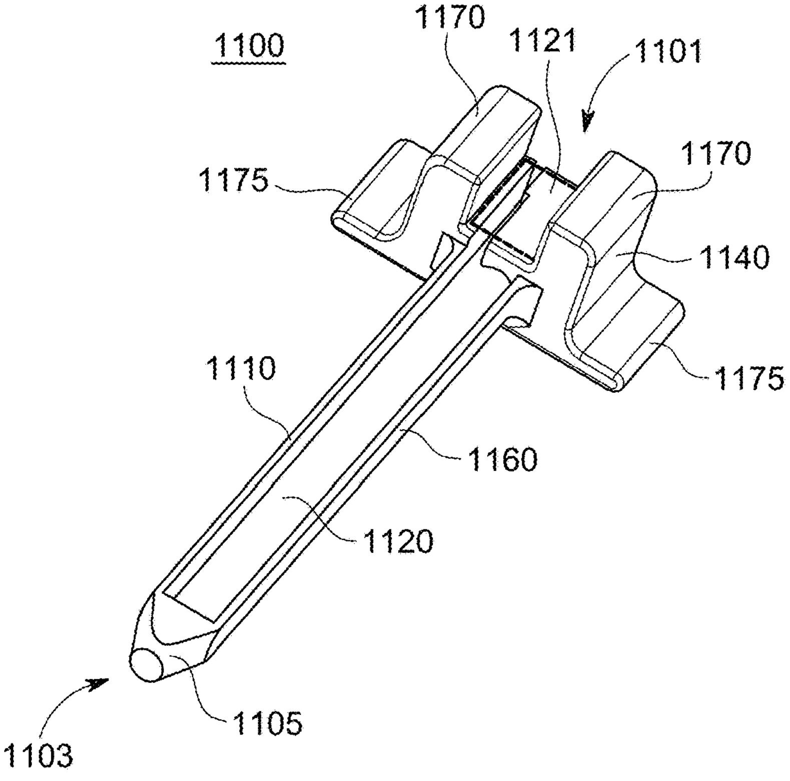
FIG. 11B is a perspective view of an additional embodiment of the surgical device showing the distal end of the device.

Further, the cannula 105 of the surgical device 100 may include the base member 113 at the proximal end 112. As will be described in more detail, the base member 113 may define a generic opening into the bore 116 within the tubular body 126 portion for slidably receiving the first surgical implement 840 and the second surgical implement, such as a forward cutting knife, reverse cutting knife or rasp, for example. As used herein, the term generic means that the opening is not side specific and it can accommodate tools for surgical procedures configured for a patient's left or right side. The base member 113 further includes a pair of wings 125 which extend in a direction perpendicular to the axial direction and provide a flat surface at a lower portion of the base member 113. This flat surface rests on the patient's body, helping to stabilize the cannula 105 during use. In addition, the upper portion 115 of the base member 113 may be a planar surface, as shown in FIGS. 1A-1B. In another embodiment, and in contrast to the upper portion 115 of the base member 113 shown in FIGS. 1A-1B, the base member 113 may instead feature a configuration as shown in FIGS. 11A-11B, with hubs 1170 that allow a physician to grip the cannula 105 more easily during use.

In addition, the surgical device 100 may also accommodate a single obturator 118 that may be positioned in the right or left orientation and may be slidably inserted through the generic opening of the base member 113 and into the bore 116 within the tubular body portion 126 of the cannula 105. The obturator 118 provides for rigidity during the initial insertion of the device 100 into the surgical incision and also prevents other soft tissue anatomy from entering into the bore 116 between the axially-extending edges 121 of the sidewall 119. In addition to the obturator 118, the surgical device 100 may also accommodate a configurable guide insert 120 that may be positioned in one of two orientations. As will be subsequently described in more detail, the configurable guide insert 120 may be inserted into and rigidly attached to the cannula 105 at an engagement point adjacent to the generic opening of the base member 113.

FIGS. 1A-1B thus show the surgical device 100 as it may be used for the initial insertion at the surgical incision, with the obturator 118 in place within the tubular body portion 126 of the cannula 105 through the generic opening of the base member 113. In the initial insertion of the device 100, the distal end 114 of the cannula 105 is inserted first in an incision. The support surface 110 contacts soft tissue structures at the surgical sight, providing support and inhibiting the soft tissue structures from blocking the bore 116, thereby limiting the potential of the soft tissue structures from contacting or impeding the view or motion of the surgical implements. Likewise, the obturator 118 prevents the entry of the soft tissue structures within the bore 116 of the tubular body 126. The cannula 105 may be formed from suitable material which is acceptable for being temporarily inserted into the human body during a surgical procedure. For example, the cannula 105 may be formed from a medically-acceptable plastic material. Metal materials are also possible. The cannula 105 may be manufactured using an opaque, translucent, or transparent material.

Figure 2A:
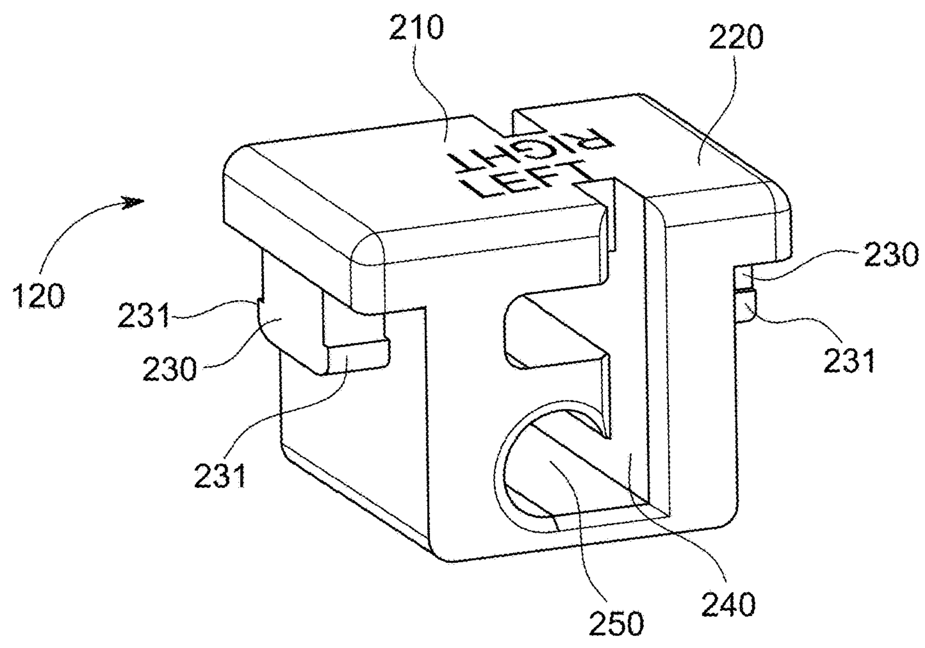
FIG. 2A is a perspective view of a configurable guide insert for use as part of the surgical device.
Figure 2B:
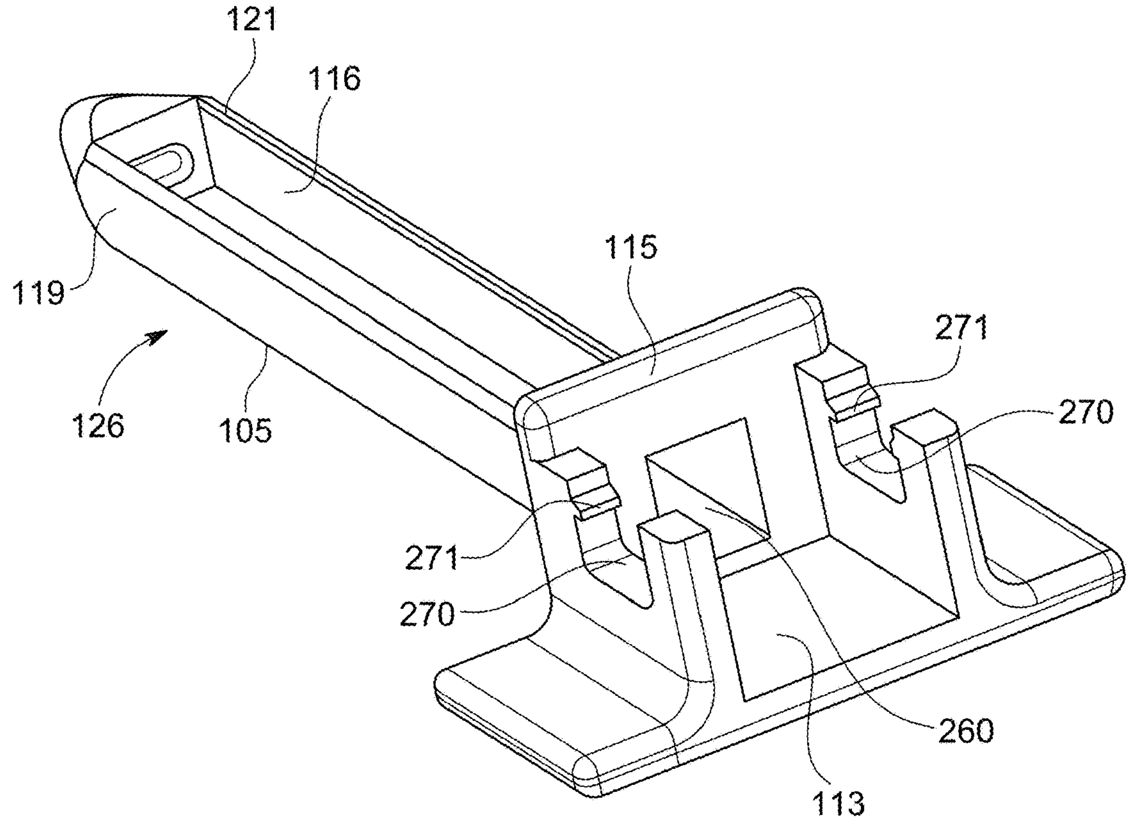
FIG. 2B is a perspective view of a cannula with generic opening for use as part of the surgical device.
Figure 2C:
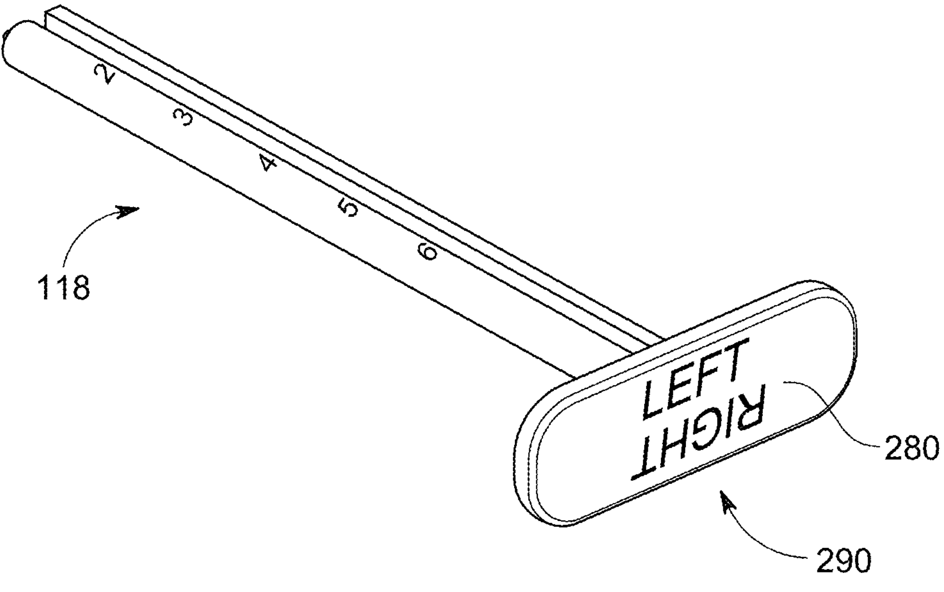
FIG. 2C is a perspective view of an obturator for use as part of the surgical device.

Referring to FIGS. 2A-2C, the three individual components of the device 100 are depicted individually. The configurable guide insert 120, as shown in FIG. 2A, may feature a singular contiguous opening including a circular opening 250 and a slot opening 240. The configurable guide insert 120 may further include a top portion 220 with markings 210, and engaging members 230 for rigidly attaching to the cannula 105 at corresponding receiving points 270 (as shown in FIG. 2B) in the base member 113. In one embodiment, the engagement members 230 on both sides of the configurable guide insert 120 are identical to each other. The receiving points 270 may include ridges 271 that couple to the corresponding ridges 231 of the engaging members 230 of the configurable guide insert 120.

The corresponding ridges 231 may be formed as an enlarged head portion of the engaging members 230, such that the engagement members have a T-shaped profile. The enlarged head portion of the engaging members 230 may be press-fit, snap-fit, or interference fit into engagement with the ridges 271 of the receiving points 270. The connection between the configurable guide insert 120 and the base member 113 of the cannula 105 is achieved via direct connection between the receiving points 270 and corresponding ridges 231. The term receiving points is used generally herein to generally refer to any shaped receptacle or opening in the base member 113. The term corresponding ridges 231 is used generally herein to refer to any shaped protrusion or arm formed on the configurable guide insert 120. Although specific geometries and configurations are illustrated in the drawings, one of ordinary skill in the art would understand based on this disclosure that any complementary shaped interface can be provided between the configurable guide insert 120 and the base member 113. No additional fastening or securing elements are required to attach the configurable guide insert 120 to the cannula 105 besides the integrally formed features formed on each of these components.

As aforementioned, the configurable guide insert 120, as shown in FIG. 2A, may feature a singular contiguous opening including a circular opening 250 and a slot opening 240, which define axially-extending spaces for receiving other components of the surgical device 100, thereby accommodating insertion of multiple surgical instruments. The circular opening 250 and slot opening 240 define the designated regions within the singular contiguous opening of the configurable guide insert 120 for the restricted positioning and movement of the surgical instruments within the configurable guide insert 120. For example, the circular opening 250 may receive a first surgical implement and the slot opening 240 may receive a second surgical implement. The surgical instruments are restricted to only stay within their respective designated regions within the singular contiguous opening through the configurable guide insert 120. More specifically, the circular opening 250 provides an opening through the configurable guide insert 120 for insertion of a camera device 840, and the slot opening 240 provides an opening through the configurable guide insert 120 for insertion of a second surgical instrument, such as a cutting implement or rasp, for example. In general, the circular opening 250 and slot opening 240 of the insert 120 may be oriented for a patient's left side or right side, as noted by the markings 210 on the top portion 220 of the configurable guide insert 120. For example, the instrument may be oriented for an incision point at the ulnar portion of a patient's left hand or right hand. The left and right orientations of the configurable guide insert 120 enable the physician to ensure that the second surgical implement that is inserted within the slot opening 240 of the insert 120 will remain away from adjacent soft tissue structures during a surgical procedure. The configurable guide insert of FIG. 2A is shown in an orientation for a procedure in the left hand of a patient.

Referring to FIG. 2B showing the tubular body portion 126 of the cannula 105 with generic opening 260 of the base member 113, the base member 113 may feature the corresponding receiving points 270 to accept and engagingly lock to the corresponding engaging members 230 of the configurable guide insert 120. As aforementioned, the receiving points 270 may include ridges 271 that couple to the corresponding ridges 231 of the engaging members 230 of the configurable guide insert 120. The upper portion 115 of the base member 113 separates the generic opening 260 from the opening defined by the bore 116 between the axially-extending edges 121 of the sidewall 119. In another embodiment of the base member 113, and in contrast to the upper portion 115 of the base member 113 shown in FIGS. 2B, the base member 113 may instead feature a configuration as shown in FIGS. 11A-11B, where the generic opening 260 and the opening defined by the bore 116 between the axially-extending edges 121 of the sidewall 119 effectively define one opening.

Referring to FIG. 2C showing the obturator 118 of the device 100, the proximal end 290 of the obturator 118 may feature markings 280 that assist the physician in orienting the obturator 118 according to whether the device 100 will be inserted into an incision point in either the left side or right side of a patient. The markings 280 may comprise letters ("L" or "R") or words ("LEFT" or "RIGHT") or may alternatively comprise anatomic references, such as "ULNAR", "RADIAL", "VOLAR" or "DORSAL". As such, the obturator 118 may interface with the device 100 and configurable guide insert 120 that is oriented for a patient's left hand or right hand, for example. The obturator 118 may be placed within the tubular body portion 126 of the cannula 105 by inserting the obturator 118 through the circular opening 250 of the configurable guide insert 120 and through the generic opening 260 of the base member 113. As described previously, the obturator 118 prevents the entry of the soft tissue structures within the bore 116 of the tubular body 126.

Figure 3A:
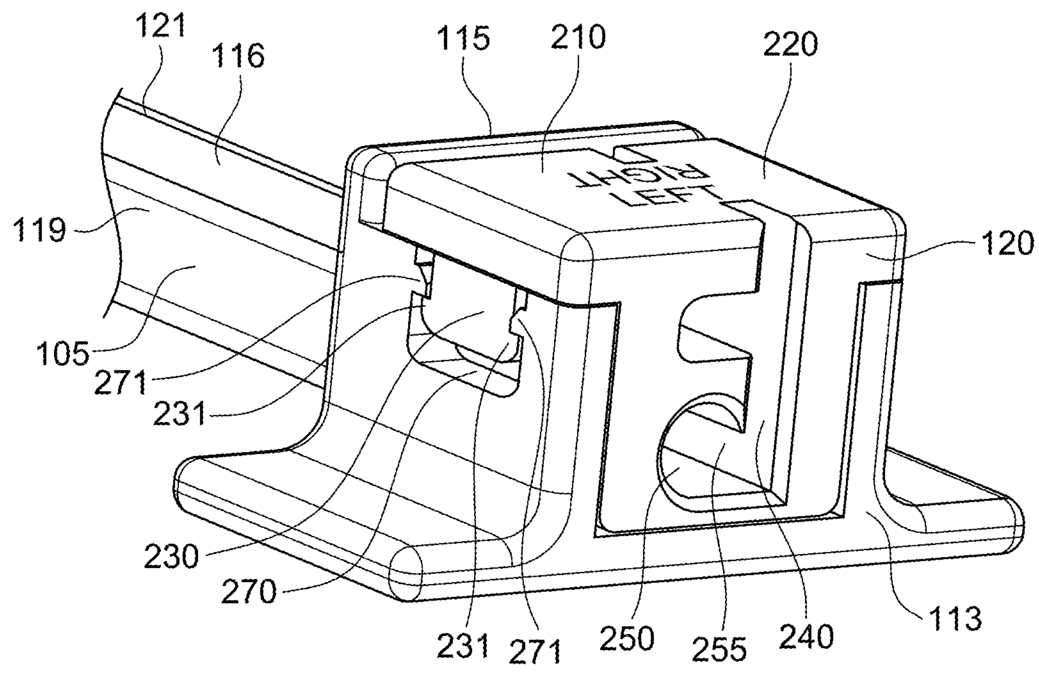
FIG. 3A is a perspective view of a configurable guide insert lockingly engaging within the base member of a cannula.

Referring to FIG. 3A showing the configurable guide insert 120 lockingly engaged within the base member 113 of the cannula 105, the corresponding receiving points 270 of the base member 113 accept and engagingly lock to the engaging members 230 of the configurable guide insert 120. In particular, the receiving points 270 may include ridges 271 that couple to the corresponding ridges 231 of the engaging members 230 of the configurable guide insert 120. Further, the base member 113 with configurable guide insert 120 in place within the base member 113 defines a combination track 255. The combination track 255 of the configurable guide insert 120 may include one contiguous opening with space to accommodate insertion of multiple surgical instruments, where the surgical instruments are restricted to only stay within their respective designated regions within the singular contiguous opening of the combination track 255 of the configurable guide insert 120. More specifically, the singular contiguous opening through the combination track 255 of the configurable guide insert 120 may include at least the circular opening 250 and the slot opening 240, which define axially-extending spaces for receiving other components of the surgical device. The circular opening 250 and slot opening 240 define the designated regions within the singular contiguous opening through the combination track 255 of the configurable guide insert 120 for the restricted positioning and movement of the surgical instruments within the combination track 255 of the configurable guide insert 120. For example, the circular opening 250 may receive a first surgical implement and the slot opening 240 may receive a second surgical implement. The circular opening 250 within the configurable guide insert 120 extends through the generic opening 260 (shown in FIG. 2B) of the base member 113 into a bore 116 for slidably receiving the first surgical implement. The slot opening 240 within the configurable guide insert 120 extends through the generic opening 260 (shown in FIG. 2B) of the base member 113 into an action area outside of and adjacent to the bore 116 for slidably receiving the second surgical implement. As used herein, an area is "outside of and adjacent to" the bore 116 when a corresponding space is non-axial with the bore 116 and adjacent to the region defined by the bore 116.

As will be described in more detail, the slot opening 240 and second surgical implement may include mating features to couple the second surgical implement to the slot opening 240 of the base member 113, which allows for guided sliding of the second surgical implement through the configurable guide insert 120 and generic opening 260 (shown in FIG. 2B) of the base member 113 into an action area adjacent to the bore 116. The first surgical implement may be a camera device 840, and the second surgical implement may be anyone one of the tissue manipulation devices 810, 820, 830 shown in FIGS. 8A-8C, which may be one of a rasp 810, reverse cutting knife 820, or forward cutting knife 830. The surgical device 100 may provide the advantage of positioning the second surgical implement laterally adjacent to the camera device 840. In particular, the surgical device 100 offers optimum visibility via the camera device 840 for the physician to view the second surgical implement during a surgical procedure. Further, the surgical device 100 also simplifies insertion of the cannula 105 at the narrow incision point since the first and second surgical implements are positioned laterally adjacent to each other, rather than in a top-to-bottom arrangement.

Referring again to FIG. 3A, the first and second surgical implement may be slidably inserted within the circular opening 250 and slot opening 240, respectively, of the combination track 255. The circular opening 250 and slot opening 240 each creates an opening so that the first surgical implement and second surgical implement may be respectively introduced through the circular opening 250 and slot opening 240 along an axis parallel to the axis of the bore 116. The circular opening 250 and slot opening 240 may be connected openings, forming an inlet through the generic opening 260 of the base member 113 to an area outside of and adjacent to the bore 116, which may be an area radially between the axially-extending edges 121 of the sidewall 119. As used herein, an area is "radially between" the edges 121 when a corresponding space is between parallel planes which pass through the edges 121. Referring again to FIG. 3A, the configurable guide insert 120 may include a top portion 220 with markings 210 to assist the user in selecting an orientation of the configurable guide insert 120 within the base member 113 of the cannula 105, for a surgical procedure in either the left or right side of a patient.

Figure 3B:
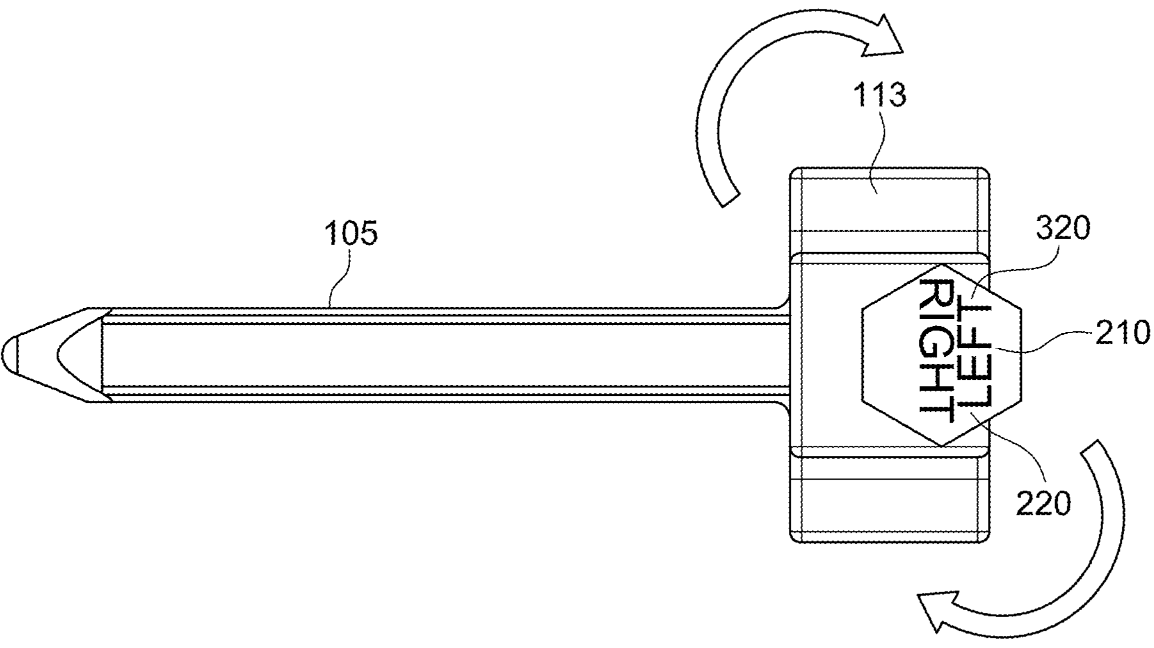
FIG. 3B is a perspective view of a configurable guide insert that is wholly contained by and attached to the base member of a cannula.

FIG. 3B provides another embodiment of the device showing a perspective view of a permanently coupled, positionable configurable guide insert 320 that is wholly contained by and attached to the base member 113 of the cannula 105. The permanently coupled, positionable configurable guide insert 320 of the embodiment in FIG. 3B is permanently coupled to the cannula 105, yet a user may rotate the configurable guide insert 320 180 degrees into place for each of the right and left orientations of the device, as indicated by the arrows in FIG. 3B. Although the permanently coupled, positionable configurable guide insert 320 shown in FIG. 3B features a hexagonal shape to accommodate the rotational functionality, one of ordinary skill in the art would understand based on this disclosure that any complementary shaped interface can be provided between the permanently coupled, positionable configurable guide insert 320 and the base member 113 of the cannula 105 to achieve the functionality to rotate the permanently coupled, positionable configurable guide insert 320 180 degrees into either the left or right orientation of the device. It is further understood that known mechanisms may be implemented to accommodate the permanent coupling of the configurable guide insert 320 to the base member 113 while also facilitating the user's ability to rotate the configurable guide insert 320 180 degrees into either the left or right orientation of the device. For example, the configurable guide insert 320 of the embodiment of FIG. 3B may be positionable for each of the left or right orientations of the device by operation of a push button (not pictured), such that a user may operate the push button or other mechanism to rotate the configurable guide insert 320 180 degrees within the base member 113 of the cannula 105, with the configurable guide insert 320 being permanently coupled to the base member 113. Of course, although the embodiment of FIG. 3B is shown in a left orientation, for a surgical procedure in a left side of a patient, a user may quickly rotate the configurable guide insert 320 into the alternative right orientation, for a surgical procedure in a right side of a patient.

Referring again to FIG. 3B in conjunction with FIG. 3A, although not shown in FIG. 3B, it is understood that the embodiment of FIG. 3B with permanently coupled, positionable configurable guide insert 320 further includes the combination track 255 with the circular opening 250 and the slot opening 240, as previously described in relation to FIG. 3A. The configurable guide insert 320 in the embodiment of FIG. 3B may include one contiguous opening with space to accommodate insertion of multiple surgical instruments, where the surgical instruments are restricted to only stay within their respective designated regions within the singular contiguous opening of the combination track 255 of the configurable guide insert 320. More specifically, the singular contiguous opening through the combination track 255 of the configurable guide insert 320 may include at least the circular opening 250 and the slot opening 240, which define axially-extending spaces for receiving other components of the surgical device. The circular opening 250 and slot opening 240 define the designated regions within the singular contiguous opening through the combination track 255 of the configurable guide insert 320 for the restricted positioning and movement of the surgical instruments within the combination track 255 of the configurable guide insert 320. For example, the circular opening 250 may receive a first surgical implement and the slot opening 240 may receive a second surgical implement. Notably, when a user rotates the configurable guide insert 320 of the embodiment of FIG. 3B 180 degrees into either the left or right orientation, the contiguous opening of the configurable guide insert 320 with circular opening 250 and slot opening 240 is axially aligned with the generic opening 260 (shown in FIG. 2B) of the base member 113 to slidably receive surgical implements into the bore 116. When a user rotates the permanently coupled, positionable configurable guide insert 320 of FIG. 3B into either the left or right orientation, the circular opening 250 may be aligned upon rotation to extend axially through the generic opening 260 (shown in FIG. 2B) of the base member 113 into the bore 116 to slidably receive the first surgical implement, and the slot opening 240 may be aligned to extend axially through the generic opening 260 (shown in FIG. 2B) of the base member 113 into an action area outside of and adjacent to the bore 116 to slidably receive the second surgical implement. As used herein, an area is "outside of and adjacent to" the bore 116 when a corresponding space is non-axial with the bore 116 and adjacent to the region defined by the bore 116.

Referring again to FIG. 3B, it is further understood that the slot opening 240 and second surgical implement may include mating features to couple the second surgical implement to the slot opening 240 of the configurable guide insert 320, which allows for guided sliding of the second surgical implement through the configurable guide insert 320 and generic opening 260 (shown in FIG. 2B) of the base member 113 into an action area adjacent to the bore 116. The first surgical implement may be a camera device 840, and the second surgical implement may be anyone one of the tissue manipulation devices 810, 820, 830 shown in FIGS. 8A-8C, which may be one of a rasp 810, reverse cutting knife 820, or forward cutting knife 830. The surgical device as shown in FIG. 3B may provide the advantage of positioning the second surgical implement laterally adjacent to the camera device 840. In particular, the surgical device offers optimum visibility via the camera device 840 for the physician to view the second surgical implement during a surgical procedure. Further, the surgical device also simplifies insertion of the cannula 105 at the narrow incision point since the first and second surgical implements are positioned laterally adjacent to each other, rather than in a top-to-bottom arrangement.

Referring again to FIG. 3B, it is understood that the first and second surgical implement may be slidably inserted within the circular opening 250 and slot opening 240, respectively, of the combination track 255. The circular opening 250 and slot opening 240 each create an opening so that the first surgical implement and second surgical implement may be respectively introduced through the circular opening 250 and slot opening 240 along an axis parallel to the axis of the bore 116. The circular opening 250 and slot opening 240 may be connected openings, forming an inlet through the generic opening 260 of the base member 113 to an area outside of and adjacent to the bore 116, which may be an area radially between the axially-extending edges 121 of the sidewall 119. As used herein, an area is "radially between" the edges 121 when a corresponding space is between parallel planes which pass through the edges 121. Referring again to FIG. 3B, the permanently coupled, positionable configurable guide insert 320 may further include a top portion 220 with markings 210 to assist the user in selecting an orientation of the permanently coupled, positionable configurable guide insert 320 within the base member 113 of the cannula 105, for a surgical procedure in either the left or right side of a patient.

Figure 4A:
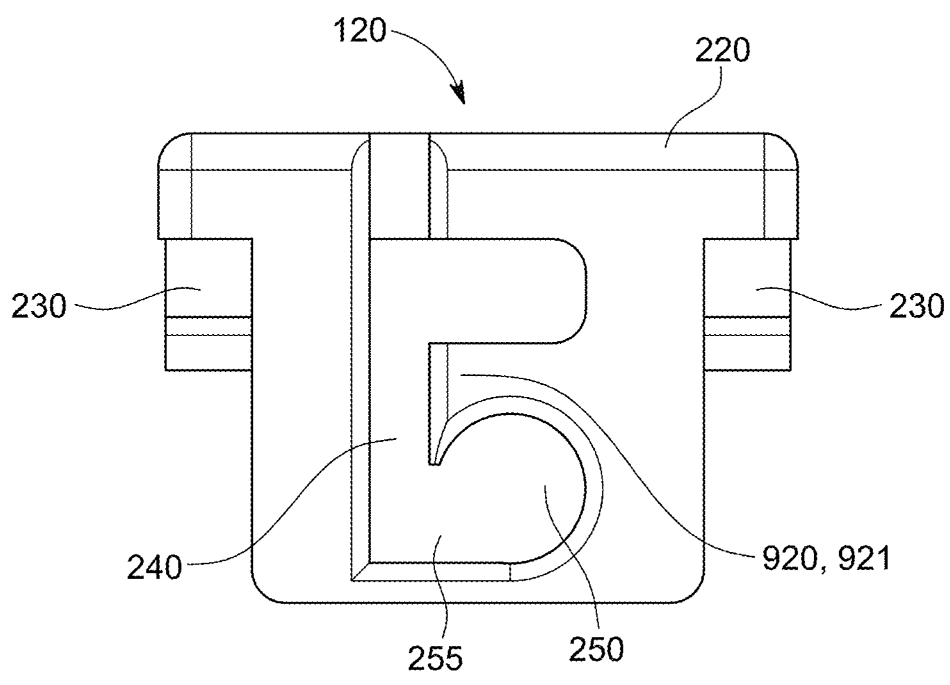
FIG. 4A is an enlarged perspective view of the proximal portion of a right orientation of the configurable guide insert.
Figure 4B:
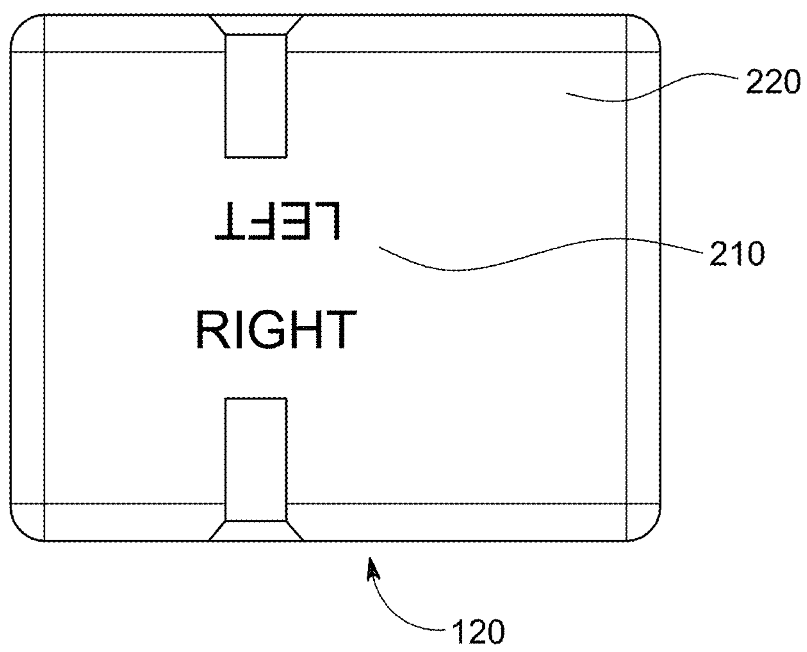
FIG. 4B is an enlarged perspective view of the top portion of a right orientation of the configurable guide insert.

Referring to FIGS. 4A-4B, the configurable guide insert 120 in the disclosed embodiments may detachably couple to the base member 113 of the cannula 105. FIGS. 4A-4B provide expanded views of a configurable guide insert 120 shown in an orientation for a procedure in the right side of a patient (e.g., the right hand), the slot opening 240 and circular opening 250 of the insert 120 may be oriented for a patient's right hand, as noted by the marking 210 on the top portion 220 of the configurable guide insert 120. As shown in the right orientation in FIGS. 4A-4B, the slot opening 240 may be positioned along the ulnar side of the patient's right wrist, so that the second surgical implement, such as a cutting instrument, that is inserted within the slot opening 240 of the configurable guide insert 120 will remain away from adjacent soft tissue structures of the right hand during a surgical procedure. Further, the expanded view provided by FIG. 4A for the configurable guide insert 120 also shows the engaging members 230 along with the combination track 255 having the circular opening 250 and slot opening 240. As will be described in further detail, the combination track 255 of the configurable guide insert 120 may also include the mating feature 920 including the protuberance 921 that matingly couples to the corresponding mating features of the second surgical implement, such as a cutting implement with a blade, for example.

Figure 5A:
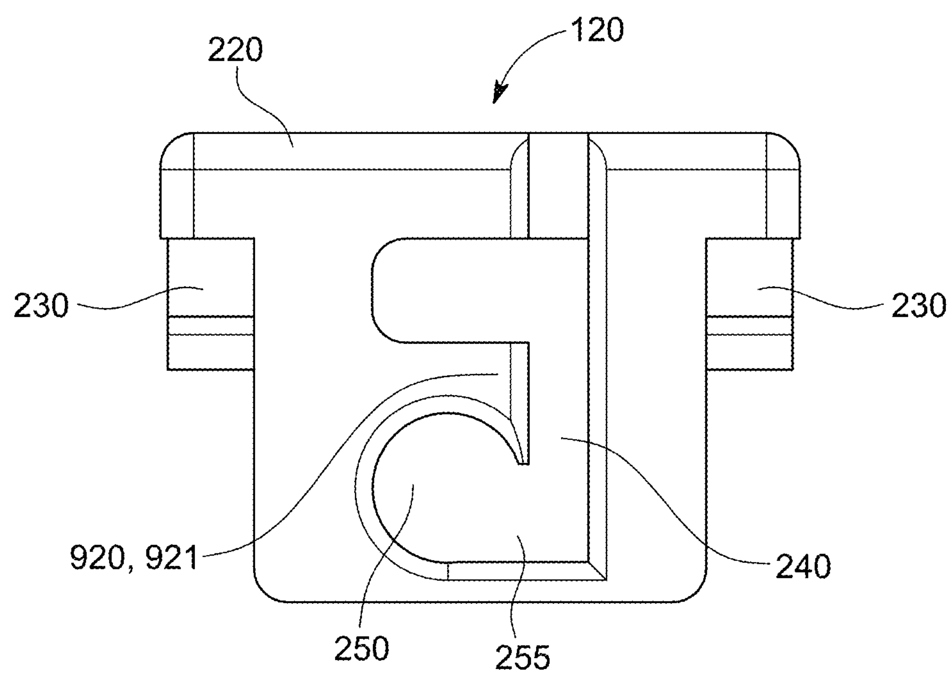
FIG. 5A is an enlarged perspective view of the proximal portion of a left orientation of the configurable guide insert.
Figure 5B:
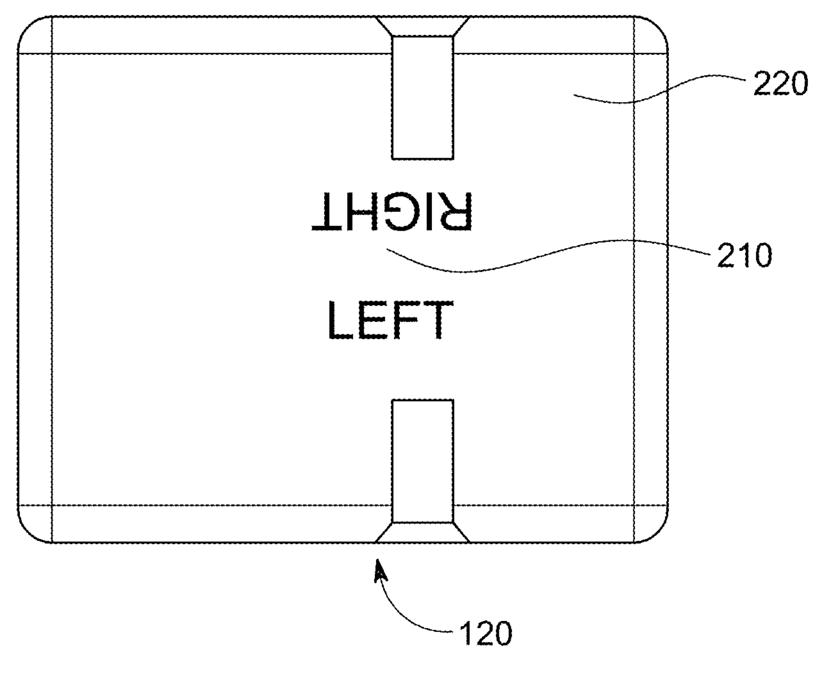
FIG. 5B is an enlarged perspective view of the top portion of a left orientation of the configurable guide insert.

Similarly, FIGS. 5A-5B provide expanded views of the configurable guide insert 120 shown in an orientation for a procedure in the left side of a patient (e.g., the left hand), the slot opening 240 and circular opening 250 of the configurable guide insert 120 may be oriented for a patient's left hand, as noted by the markings 210 on the top portion 220 of the insert 120. As shown in the left orientation in FIGS. 5A-5B, the slot opening 240 may be positioned along the ulnar side of the patient's left wrist, so that the second surgical implement, such as a cutting instrument, that is inserted within the slot opening 240 of the configurable guide insert 120 will remain away from adjacent soft tissue structures of the left hand during a surgical procedure. Further, the expanded view provided by FIG. 5A for the configurable guide insert 120 also shows the engaging members 230 along with the combination track 255 having the circular opening 250 and slot opening 240. As will be described in further detail, the combination track 255 of the configurable guide insert 120 may also include the mating feature 920 including the protuberance 921 that matingly couples to the corresponding mating features of the second surgical implement, such as a cutting implement with a blade, for example.

Figure 6A:
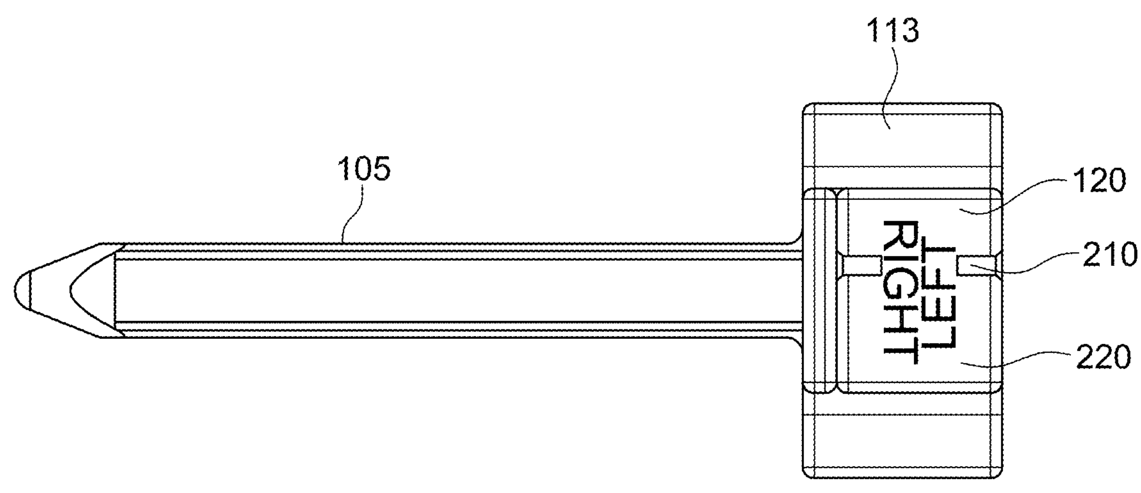
FIG. 6A is a top perspective view of a left orientation of a configurable guide insert lockingly engaging within the base member of a cannula.
Figure 6B:
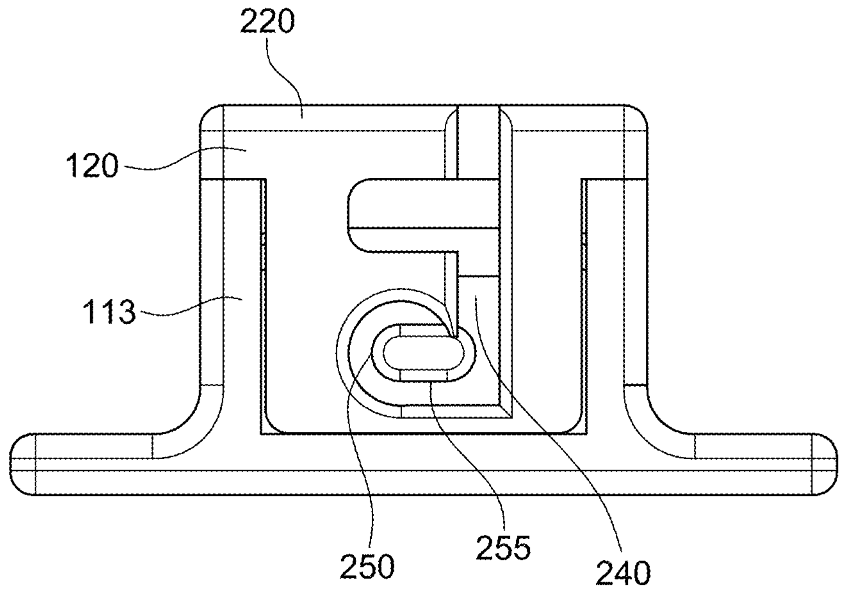
FIG. 6B is a proximal perspective view of a left orientation of a configurable guide insert lockingly engaging within the base member of a cannula.
Figure 6C:
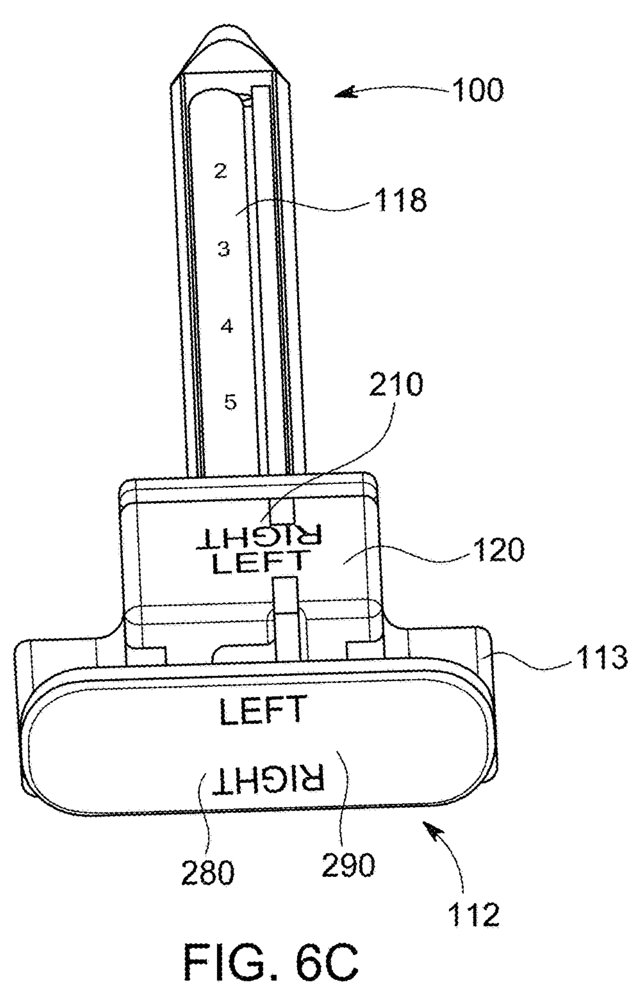
FIG. 6C is a proximal perspective view of a left orientation of both an obturator and a configurable guide insert within the base member of a cannula.
Figure 6D:
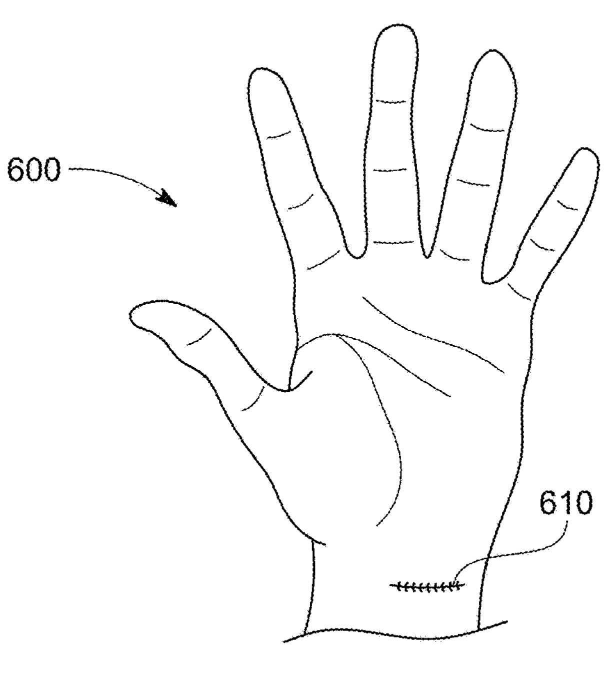
FIG. 6D is a perspective view of a patient's left hand showing an incision point for a left orientation of the surgical device.

FIGS. 6A-6D provide additional views of the configurable guide insert 120 in a left orientation within the base structure 113 of the cannula 105. When the configurable guide insert 120 is lockingly engaged within the base structure 113 in the left orientation, the markings 210 on the top portion 220 of the configurable guide insert 120 may indicate a letter ("L") or word ("LEFT") or an anatomic reference, such as "ULNAR", "RADIAL", "VOLAR" or "DORSAL". In particular, the markings 210 on the top portion 220 of the configurable guide insert 120 indicate the correct orientation of the device 100 for the left orientation when the device 100 is viewed from the proximal end 112 of the device 100. For example, as shown in FIG. 6C, when viewing the device 100 from the proximal end 112, the markings 210 on the top portion 220 of the configurable guide insert 120 indicate "LEFT" so that the physician knows that the device 100 will be inserted into an incision point 610 in the ulnar side of a patient's left hand 600, as shown in FIG. 6D. In the left orientation shown in FIGS. 6A-6C, the second surgical implement, such as a cutting instrument that is inserted within the slot opening 240 of the configurable guide insert 120, will remain away from adjacent soft tissue structures of the left hand 600 during a surgical procedure. Although FIG. 6D provides an illustration of a patient's left hand, it is understood that the device 100 may be utilized for surgical procedures at incision points within additional anatomical locations of the body, such as a left foot, for example.

Figure 7A:
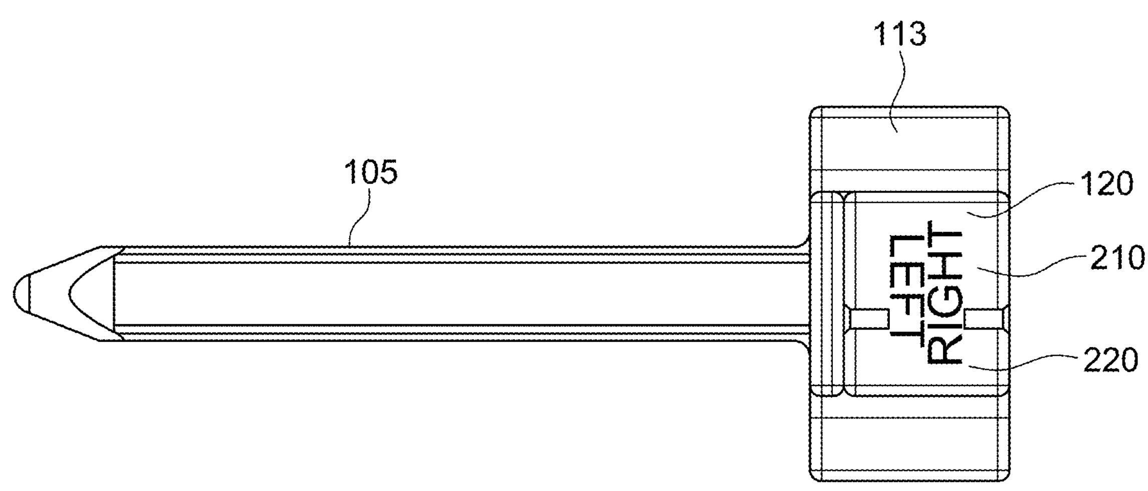
FIG. 7A is a top perspective view of a right orientation of a configurable guide insert lockingly engaging within the base member of a cannula.
Figure 7B:
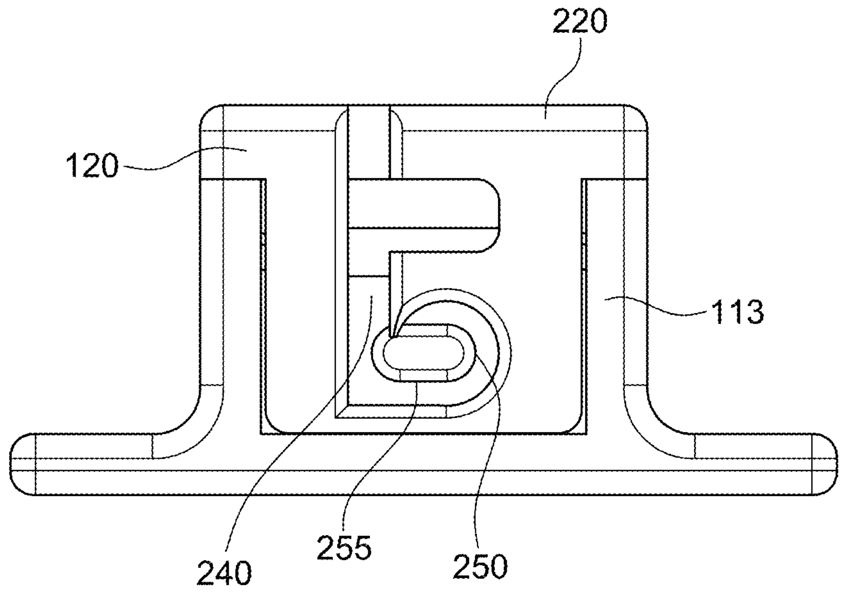
FIG. 7B is a proximal perspective view of a right orientation of a configurable guide insert lockingly engaging within the base member of a cannula.
Figure 7C:
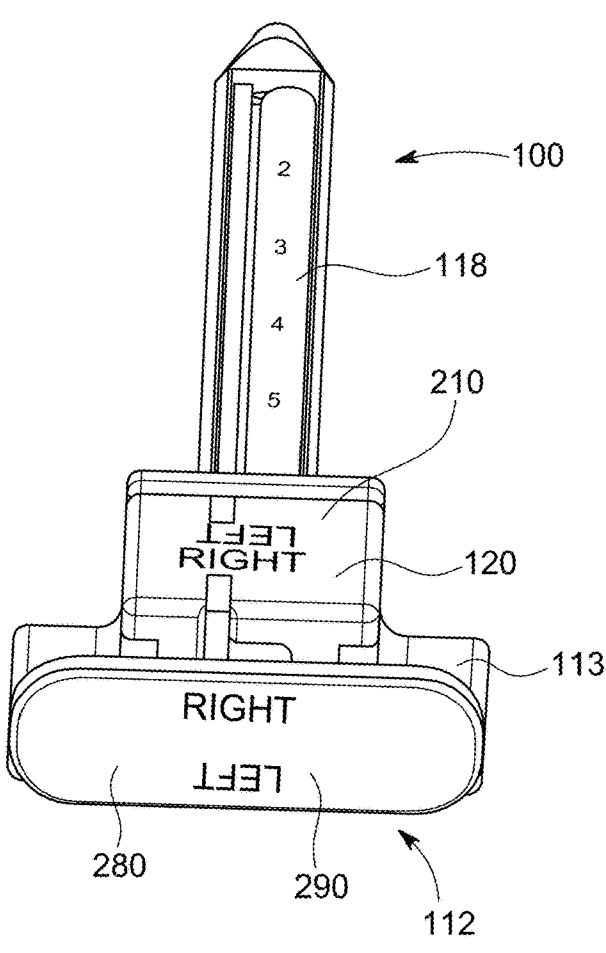
FIG. 7C is a proximal perspective view of a right orientation of both an obturator and a configurable guide insert within the base member of a cannula.
Figure 7D:
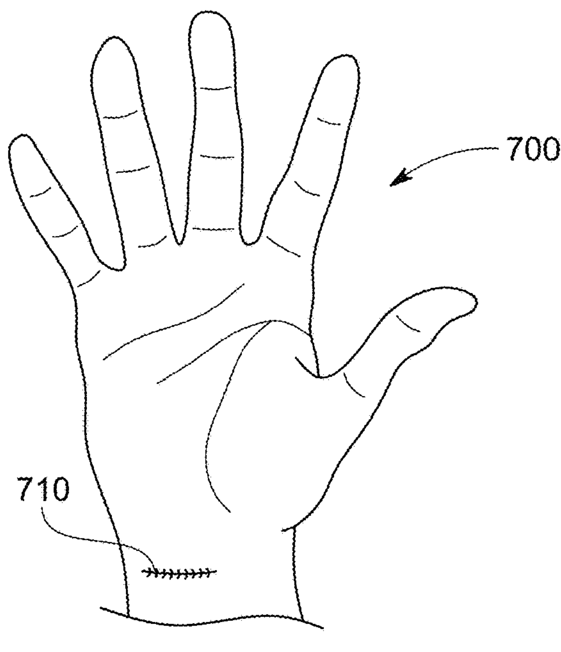
FIG. 7D is a perspective view of a patient's right hand showing an incision point for a right orientation of the surgical device.

Similarly, FIGS. 7A-7D provide additional views of the configurable guide insert 120 in a right orientation within the base structure 113 of the cannula 105. When the configurable guide insert 120 is lockingly engaged within the base structure 113 in the right orientation, the markings 210 on the top portion 220 of the configurable guide insert 120 may indicate a letter ("R") or word ("RIGHT") or an anatomic reference, such as "ULNAR", "RADIAL", "VOLAR" or "DORSAL". In particular, the markings 210 on the top portion 220 of the configurable guide insert 120 indicate the correct orientation of the device 100 for the right orientation when the device 100 is viewed from the proximal end 112 of the device 100. For example, as shown in FIG. 7C, when viewing the device 100 from the proximal end 112, the markings 210 on the top portion 220 of the configurable guide insert 120 indicate "RIGHT" so that the physician knows that the device 100 will be inserted into an incision point 710 in the ulnar side of a patient's right hand 700, as shown in FIG. 7D. In the right orientation shown in FIGS. 7A-7C, the second surgical implement, such as a cutting instrument, that is inserted within the slot opening 240 of the configurable guide insert 120, will remain away from adjacent soft tissue structures of the right hand 700 during a surgical procedure. Although FIG. 7D provides an illustration of a patient's right hand, it is understood that the device 100 may be utilized for surgical procedures at incision points within additional anatomical locations of the body, such as a right foot, for example.

Based on the shape of the obturator 118 (shown in FIG. 2C) relative to the shapes of the circular opening 250 and slot opening 240 of the configurable guide insert 120 (as shown in FIG. 3A), it is not possible to insert the device 100 with obturator 118 in the "right" configuration for a surgical procedure in the right hand of a patient while the configurable guide insert 120 is oriented for the "left" configuration, as shown in FIGS. 6A-6C. Similarly, it is not possible to insert the device 100 with obturator 118 in the "left" configuration for a surgical procedure in the left hand of a patient while the configurable guide insert 120 is oriented for the "right" configuration, as shown in FIGS. 7A-7C. The obturator 118 must be inserted in the same configuration (i.e., left or right) as the configurable guide insert 120 based upon the shape of the obturator 118 in relation to the shapes of the circular opening 250 and slot opening 240 of the configurable guide insert 120

As aforementioned, the configurable guide insert 120 may be detachably coupled to the base member 113 of the cannula 105 in a left or right orientation with respect to a patient's left or right hand, for example. As used herein, the term detachably coupled means that the configurable guide insert 120 is rigidly attached to the base member 113 of the cannula 105 so that it can accommodate tools for surgical procedures in either a patient's left or right side, depending on whether the configurable guide insert 120 is detachably coupled to the base member 113 in a left or right orientation. Markings 210 on the configurable guide insert 120 indicate the orientation of the device 100, so that the physician may quickly assemble the device 100 by detachably coupling the configurable guide insert 120 to the base member 113 of the cannula 105, for a rigid attachment of the cannula 105, configurable guide insert 120 and obturator 118, in the selected orientation, for insertion of the device 100 at a designated incision point in a left side or right side of a patient. When detachably coupling the configurable guide insert 120 in either the "left" orientation or the "right" orientation, the configurable guide insert 120 may be rotated 180 degrees relative the axis defined by the cannula 105 and bore 116. When the configurable guide insert 120 is detachably coupled to the base member 113 in either the left or right orientation, an imaginary axis extends through the circular opening 250 of the configurable guide insert 120 and into the bore 116, and another imaginary axis extends through the slot opening 240 of the configurable guide insert 120 and into the bore 116. The configurable guide insert 120 may be quickly rotated at the time of the surgical procedure to detachably couple the configurable guide insert 120 to the base member 113 of the cannula 105 in either the left or right orientation for assembly of the device 100.

In general, each of the surgical implements may be slidably received in the combination track 255 of the configurable guide insert 120, when the configurable guide insert is lockingly engaged within the base member 113 of the surgical device 100. FIGS. 8A-8C illustrate a camera device 840 and tissue manipulation devices 810, 820, 830. In one embodiment, the tissue manipulation devices 810, 820, 830 may be one of a rasp 810, reverse cutting knife 820, or forward cutting knife 830, as shown in FIGS. 8A-8C. When the tissue manipulation devices 810, 820, 830 are used in conjunction with the surgical device 100, the second surgical implement may be any of the tissue manipulation devices 810, 820, 830.

Referring again to FIGS. 8A-8C in conjunction with FIG. 3A, in use, the camera device 840 slides through the first section 250 of the combination track 255, into the bore 116 until it reaches the distal end 114 (shown in FIGS. 1A-1B) of the device 100. The camera device 840 thereby supplies a visualization of a target tissue at which the distal end 114 is positioned in a patient. The opening of the bore 116 at the distal end 114 provides an axial line of sight for the camera device 840 while the opening formed by the sidewall 119 provides a radial line of sight. The tissue manipulation device slides through the slot opening 240 of the combination track 255, adjacent to the camera device 840. The slot opening 240 guides the tissue manipulation device such that the surgical procedure may be carried out with assistance from the visualization provided by the camera device 840.

As seen in FIGS. 8A-8C, the tissue manipulation devices 810, 820, 830 may include various features, including, for example, acting features 811, 821, 831, sliding features, and handle features 851, 852, 853. The acting features 811, 821, 831 are components (e.g., blade, clamp, hook, etc.) which are capable of completing a surgical task (e.g., cutting, moving, modifying, etc.). The sliding features include a structure which interacts with the cannula 105 to allow the tissue manipulation devices 810, 820, 830 to be guided relative to the camera device 840. The handle features 851, 852, 853 are, for example, upwardly-extending handles which allow a physician to easily grasp and move the tissue manipulation devices 810, 820, 830.

Figure 9:
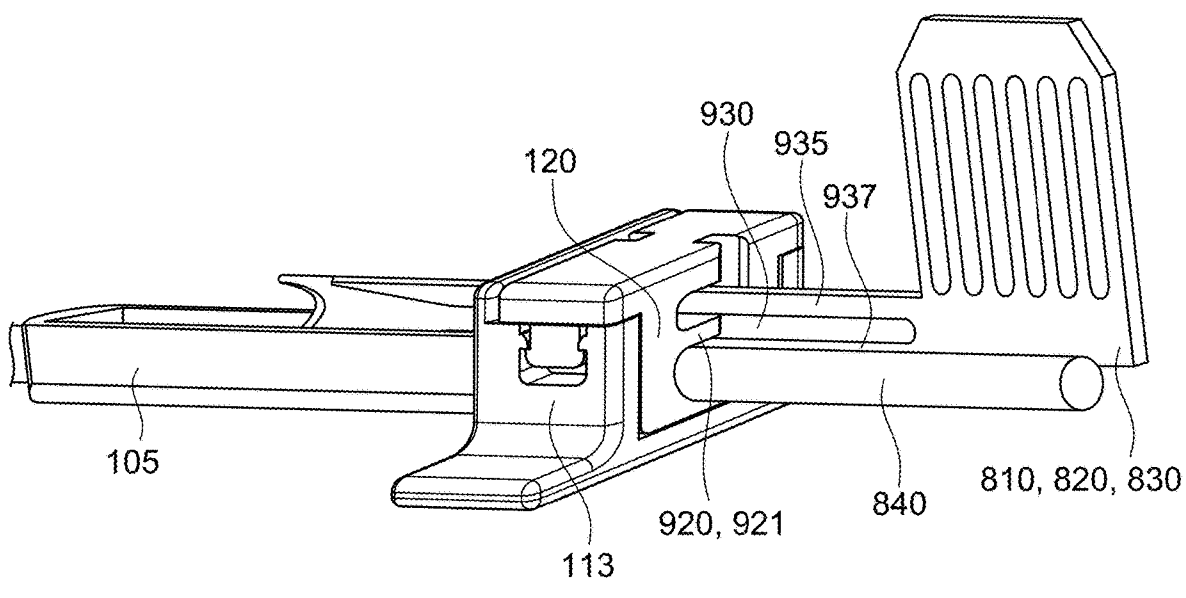
FIG. 9 is a perspective view of the surgical device of FIGS. 1A-1C with forward cutting knife and camera device inserted within the surgical device.

Focusing now on the interplay between the camera device 840, tissue manipulation devices 810, 820, 830 and the combination track 255, in some embodiments, such as that of FIG. 9, the combination track 255 includes a mating feature 920, which couples to the corresponding mating feature 930 of the second surgical implement. As aforementioned in reference to FIGS. 8A-8C, the second surgical implement may be any of the tissue manipulation devices 810, 820, 830.

Referring again to FIG. 9, in general, the second surgical implement 810, 820, 830 includes a mating feature 930 which allows for guided sliding of the second surgical implement in the combination track 255 (as shown in FIG. 3A). FIG. 9 illustrates a forward cutting knife 830 (as shown in FIG. 8C), which includes a respective mating feature 930 formed as part of the sliding feature and which corresponds to the mating feature 920 in the combination track 255 of the configurable guide insert 120. The respective mating feature 930 of the forward cutting knife 830 couples to the corresponding mating feature 920 of the combination track 255 to provide a guide structure, which helps to control and limit the sliding action of the second surgical implement. Although the second surgical implement in FIG. 9 is shown as a forward cutting knife 830, it is understood that the second surgical implement may be any of the tissue manipulation devices 810, 820, 830 shown in FIGS. 8A-8C.

Referring again to FIG. 9, the mating feature 920 in the combination track 255 of the configurable guide insert 120 includes a protuberance 921 formed by the configurable guide insert 120. The mating feature 930 for the second surgical implement, shown in FIG. 9 as a forward cutting knife 830, includes oppositely-disposed protuberances 935, 937 formed by the body of the forward cutting knife 830, which create the corresponding mating feature and groove 930. As shown in FIG. 9, the protuberance 921 in the combination track 255 of the configurable guide insert 120 is received in the groove 930 of the forward cutting knife 830, such that the configurable guide insert 120 and the forward cutting knife 830 are interlocked for guided sliding of the forward cutting knife 830. It is understood that the combination track 255 of the configurable guide insert 120 that is lockingly engaged within the base member 113 of the surgical device 100 may be used in combination with any one of the tissue manipulation devices 810, 820, 830 shown in FIGS. 8A-8C for guiding sliding movement. In addition, it should be understood that the illustrated configurations of the mating feature 920 in the combination track 255 of the configurable guide insert 120 are exemplary and that other configurations which allow for guided sliding of the second surgical implement relative to the cannula 105 are possible.

For example, other grooves and/or protuberance combinations may be implemented to guide the sliding movement.

Referring again to FIG. 9, the mating feature 920 of the slot opening 240 in the combination track 255 (as shown in FIG. 3A) of the configurable guide insert 120 couples to the corresponding mating feature 930 of the second surgical implement to allow independent axial motion relative to the cannula 105 of the second surgical implement during the surgical procedure. Further, the mating feature 920 of the slot opening 240 in the combination track 255 limits the translation of the second surgical implement relative to the fixed position of the cannula 105, in one or more degrees of freedom. In addition, the first surgical implement 840, such as a camera device, may move independently of the cannula 105 in an axial position through the circular opening 250 in the combination track 255 (as shown in FIG. 3A) of the configurable guide insert 120, yet the circular opening 250 in the combination track 255 also limits the translation of the camera device 840, from side to side and from top to bottom, within the cannula 105. Thus, the combination track 255 of the configurable guide insert 120 provides for simultaneous, guided, axial movement for each of the second surgical implement and camera device 840 within and independent of the cannula 105.

Figure 10A:
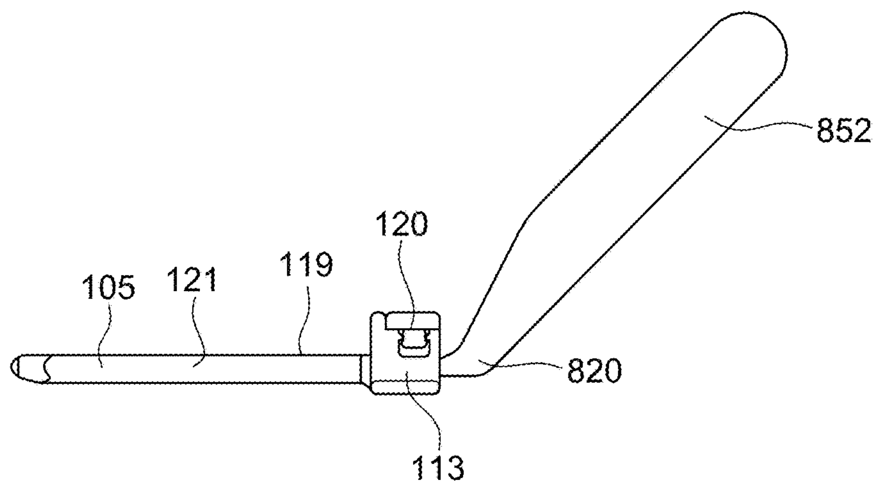
FIG. 10A is a side view of the surgical device of FIGS. 1A-1B showing a reverse cutting knife in its fully inserted position within the cannula of the surgical device.
Figure 10B:
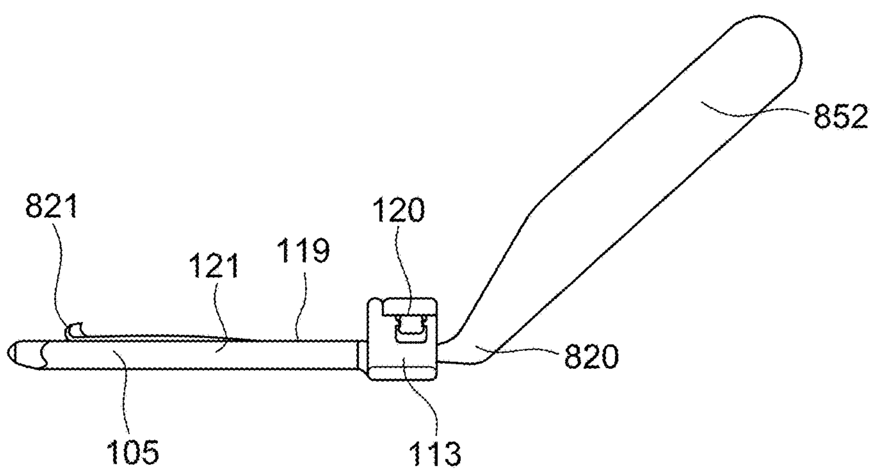
FIG. 10B is a side view of the surgical device of FIGS. 1A-1B showing a reverse cutting knife in an elevated position within the cannula of the surgical device.
Figure 10C:
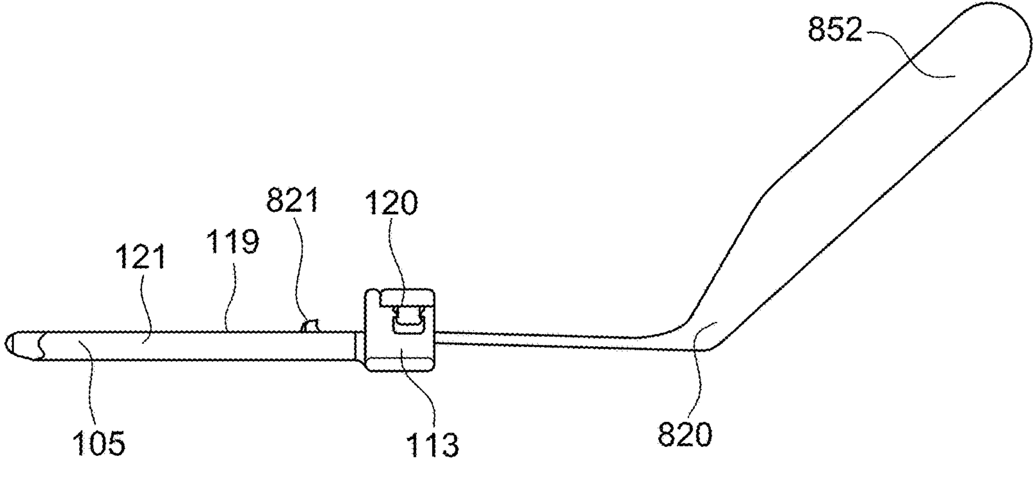
FIG. 10C is a side view of the surgical device of FIGS. 1A-1B showing a reverse cutting knife in an elevated and retracted position within the cannula of the surgical device.

Turning to FIGS. 10A-10C, side views of the cannula 105 are provided showing the positioning of an exemplary reverse cutting knife 820 in relation to its independent movement with respect to the cannula 105. As seen in FIG. 10A, once the reverse cutting knife 820 is fully inserted into the configurable guide insert 120 and base member 113 of the cannula 105, the physician may manipulate the handle feature 852 to move the cutting blade 821 of the reverse cutting knife 820 into a better position to cut target tissue, as shown in FIG. 10B. When the physician manipulates the handle 852 so that the cutting blade 821 extends above the axially-extending edges 121 of the sidewall 119 of the cannula 105, the cutting blade 821 may easily engage with soft tissue as the reverse cutting knife 820 is pulled backward out of the cannula 105, as shown in FIG. 10C.

Referring to FIG. 9 in conjunction with FIGS. 1A-1B, in use, once the physician inserts the cannula 105 with obturator 118 of the surgical device 100 at the incision point, the second surgical implement, which may be any one of the tissue manipulation devices 810, 820, 830 shown in FIGS. 8A-8C, is positioned laterally adjacent to the camera device 840. Depending on whether the configurable guide insert 120 is oriented for insertion of the device 100 within a patient's left or right hand, the second surgical implement may be positioned on either side of the camera device 840. The camera device 840 may be inserted via the circular opening 250 within the combination track 255 of the configurable guide insert 120, and the second surgical implement may be inserted via the slot opening 240 within the combination track 255 of the configurable guide insert 120.

FIGS. 11A-11B illustrate another embodiment of the surgical device 1100 consistent with the disclosed embodiments. The surgical device 1100 includes the herein-described features of the surgical device 100 with cannula 105. The surgical device 1100 may include a cannula 1110, having a proximal end 1101 and a distal end 1103 along an axial direction of the cannula 1110, and a bore 1120 extending along the axial direction through the cannula 1110. The cannula 1110 includes a base member 1140 at the proximal end 1101, a support surface 1105 at the distal end 1103, and a tubular body portion 1160 formed therebetween. The bore 1120 may extend an entire length of the cannula 1110.

In addition, the base member 1140 includes hubs 1170 formed on opposing sides of a combination track 1180 defined by a configurable guide insert 1121 (as indicated by the projected lines in FIGS. 11A-11B). The configurable guide insert 1121 may detachably couple to the base member 1140. The combination track 1180 of the configurable guide insert 1121 may include a circular opening 1185 formed as an opening into the bore 1120 for slidably receiving the first surgical implement. The combination track 1180 further includes a slot opening 1190 formed as an opening into an area adjacent to the bore 1120 for slidably receiving the second surgical implement. The circular opening 1185 and slot opening 1190 of the configurable guide insert 1121 may be oriented for a patient's left side or right side, as noted by markings (not shown) on the configurable guide insert 1121. Further, the hubs 1170 allow a physician to grip the cannula 1110 more easily during use. The base member 1140 further includes a pair of wings 1175 which extend in a direction perpendicular to the axial direction and provide a flat surface at a lower portion of the base member 1140. This flat surface rests on the patient's body, helping to stabilize the cannula 1110 during use.

Referring again to FIGS. 11A-11B, the first surgical implement may be a camera device 840 as shown in FIGS. 8A-8C, and the second surgical implement 810, 820, 830 may be any of the surgical implements shown in FIGS. 8A-8C, such as a rasp 810, reverse cutting knife 820, or forward cutting knife 830. Similar to the embodiment detailed in FIG. 9, the slot opening 1190 and second surgical implement may include mating features to couple the second surgical implement to the slot opening 1190 of the base member 1140, which allows for guided sliding of the second surgical implement 810, 820, 830. The surgical device 1100 as shown in FIGS. 11A-11B may provide the advantage of positioning the second surgical implement 810, 820, 830 laterally adjacent to the first surgical implement 840. Depending on whether the configurable guide insert 1121 of the surgical device 1100 is oriented for insertion of the cannula 1110 within a patient's left or right hand, the second surgical implement 810, 820, 830 may be positioned on either side of the camera device 840. The camera device 840 may be inserted via the circular opening 1185 within the combination track 1180 of the configurable guide insert 1121, and the second surgical implement 810, 820, 830 may be inserted via the slot opening 1190 within the combination track 1180 of the configurable guide insert 1121. In particular, the surgical device 1100 offers optimum visibility via the camera device for the physician to view the second surgical implement 810, 820, 830 during a surgical procedure. Further, the surgical device 1100 also simplifies insertion of the cannula 1110 at the narrow incision point since the first and second surgical implements 810, 820, 830 are positioned laterally adjacent to each other, rather than in a top-to-bottom arrangement. In addition, the surgical device 1100 may also accommodate an obturator 118 (as shown in FIG. 2C) that may be slidably inserted through the circular opening 1185 within the combination track 1180 of the configurable guide insert 1121 placed within the base member 1140. The obturator 118 may be advanced into the bore 1120 and positioned within the tubular body portion 1160 of the cannula 1110. The obturator 118 provides for rigidity during the initial insertion of the device 1100 into the surgical incision and also prevents other soft tissue anatomy from entering into the bore 1120 between the axially-extending edges of the sidewall.

Referring to FIGS. 1A-1B and 11A-11B, the disclosed embodiments provide a surgical device 100, 1100 which may be used in a surgical procedure. The procedure may be, for example, a soft tissue release, such as an endoscopic carpal ligament release surgery, commonly referred to as an endoscopic carpal tunnel release. Other examples include, without limitation, an endoscopic cubital tunnel release, endoscopic gastrocnemius release, endoscopic plantar fascia release, and the like. These procedures generally include the insertion of the disclosed surgical device 100, 1100 with cannula 105, 1110 into the patient, with the distal end 114, 1103 being positioned near a target tissue. The support surface 110, 1105 provides a buffer for the bore 116, 1120, helping to separate soft tissue and inhibiting the soft tissue structures from blocking a path formed by the bore 116, 1120. A configurable guide insert 120, 1121 may couple to the base member 113, 1140, where the configurable guide insert 120, 1121 defines a combination track 255, 1180 having a circular opening 250, 1185 formed as an opening into a bore 116, 1120 for slidably receiving the first surgical implement. The combination track 255, 1180 further includes the slot opening 240, 1190 formed as an opening into an area adjacent to the bore 116, 1120 for slidably receiving the second surgical implement. The circular opening 250, 1185 and slot opening 240, 1190 of the configurable guide insert 120, 1121 may be oriented for a patient's left side or right side, as noted by the markings on the configurable guide insert 120, 1121. For example, the device 100, 1100 may be oriented for an incision point at the ulnar portion of a patient's left hand or right hand. The left and right orientations of the configurable guide insert 120, 1121 enable the physician to ensure that the second surgical implement that is inserted within the slot opening 240, 1190 of the configurable guide insert 120, 1121 will remain away from adjacent soft tissue structures during a surgical procedure. A camera device 840 may be inserted into the circular opening 250, 1185 of the combination track 255, 1180 as a first surgical implement. The camera device 840 slides through a bore 116, 1120 until it reaches the distal end 114, 1103 and provides a visualization of the target tissue. A tissue manipulation device, as a second surgical implement 810, 820, 830, is then inserted into a slot opening 240, 1190 of the combination track 255, 1180 and is guided by the corresponding surfaces of a base member 113, 1140 forming the combination track 255, 1180. The guided movement of the second surgical implement 810, 820, 830 allows for controlled use of an acting feature 811, 821, 831 of the respective second surgical implement 810, 820, 830, such as to cut, excise, or modify the target tissue. The slot opening 240, 1190 and second surgical implement 810, 820, 830 may include mating features which help to guide the movement. The mating features may include various configurations which help to control the sliding movement. Moreover, the mating features may be configured such that a variety of different surgical implements may be used in combination with the same cannula 105, 1110. The surgical device 100, 1100 of the herein disclosed embodiments may be provided to the physician at the time of surgery in a single kit that includes the cannula 105, 1110, configurable guide insert 120, 1121 and obturator 118. The sterile packaged kit may be assembled at the time of an operation and configured in the desired orientation for targeting of soft tissue in a patient's left or right side, including a left or right hand.

The presently disclosed embodiments with cannula for a camera device and tissue manipulation device, where the tissue manipulation device is positioned laterally adjacent to the camera, may reduce the height of the cannula to simplify insertion of the cannula at the narrow incision point while also improving the physician's visibility of the surgical implements via the camera device. Having the tissue manipulation devices positioned laterally adjacent to the camera, rather than in a top-to-bottom relationship, relative to the camera, may provide significant advantages to both the physician and patient. Having the surgical implements positioned laterally adjacent to the camera may provide for less pain and aggravation to the patient during insertion of the cannulas 105, 1110 and greater accuracy and precision for the physician with the enhanced visibility of the surgical implements during the surgical procedure.

In addition, the presently disclosed embodiments may provide a more accurate and repeatedly consistent method of modifying soft tissue structures. The disclosed embodiments may prescribe a predefined motion for tissue manipulation devices, which helps to ensure the appropriate soft tissue structure is manipulated by the appropriate amount, and helps to prevent unwanted manipulation of adjacent soft tissue structures. The disclosed embodiments may prevent excessive or inadvertent motion of tissue manipulation devices by guiding movement thereof. The disclosed embodiments may also allow independent motion of implements and a camera device during the surgical procedure, while being in close proximity to each other. The disclosed surgical device facilitates simplified surgical steps and may provide consistency as multiple types of implements may be passed through the cannula.

Having thus described the presently preferred embodiments in detail, it is to be appreciated and will be apparent to those skilled in the art that many physical changes, only a few of which are exemplified in the detailed description of the invention, could be made without altering the inventive concepts and principles embodied therein. It is also to be appreciated that numerous embodiments incorporating only part of the preferred embodiment are possible which do not alter, with respect to those parts, the inventive concepts and principles embodied therein. The present embodiments and optional configurations are therefore to be considered in all respects as exemplary and/or illustrative and not restrictive, of the scope of the invention being indicated by the appended claims rather than by the foregoing description, and all alternate embodiments and changes to this embodiment which come within the meaning and range of equivalency of said claims are therefore to be embraced therein.

What is claimed is:

1. A cannula for use as part of a surgical device, comprising:

a base member at a proximal end;

a sidewall connected to the base member and extending in an axial direction from the proximal end to a distal end;

a bore extending in the axial direction defined by the base member and the sidewall, the sidewall further defining an opening into the bore between axially-extending edges of the sidewall; and a configurable guide insert coupled to the base member;

wherein the configurable guide insert includes a combination track including a circular opening and a slot opening, the circular opening extending through the configurable guide insert providing passage through the base member into the bore and the slot opening extending through the configurable guide insert providing passage through the base member into an action area outside the opening into the bore and radially between the edges of the sidewall;

wherein the combination track is configured to slidably receive a first surgical implement through the circular opening and into the bore and slidably receive a second surgical implement through the slot opening and into the action area;

wherein the configurable guide insert is coupled to be positionable in a configurable orientation comprising a right orientation for positioning of the first and second surgical implements for a surgical procedure in a right side of a patient, or a left orientation for positioning of the first and second surgical implements for the surgical procedure in a left side of the patient;

wherein the configurable guide insert is configured for rotation of 180 degrees about an axis defined in relation to the cannula when positioning the configurable guide insert on the base member in the right orientation or in the left orientation; and wherein the configurable guide insert includes a set of markings configured to indicate whether the configurable guide insert is coupled to the base member in the right orientation for the surgical procedure in the right side of the patient or in the left orientation for the surgical procedure in the left side of the patient.

2. The cannula of claim 1, wherein the axis defined in relation to the cannula is parallel or equal to a longitudinal axis defined by the cannula.

3. The cannula of claim 2, wherein the configurable guide insert further comprises a push button configured to rotate the configurable guide insert for rotation of 180 degrees about an axis perpendicular to the longitudinal axis defined by the cannula when positioning the configurable guide insert on the base member in the right orientation or in the left orientation.

4. The cannula of claim 1, wherein the axis defined in relation to the cannula is perpendicular to a longitudinal axis defined by the cannula.

5. The cannula of claim 4, wherein the configurable guide insert further comprises a push button configured to rotate the configurable guide insert for rotation of 180 degrees about an axis parallel to the longitudinal axis defined by the cannula when positioning the configurable guide insert on the base member in the right orientation or in the left orientation.

6. The cannula of claim 1, wherein the configurable guide insert is rigidly locked into the configurable orientation.

7. The cannula of claim 1, wherein the first surgical implement is a camera device and the second surgical implement is a tissue manipulation device, the tissue manipulation device including a surgical blade configured to cut soft tissue.

8. The cannula of claim 1, wherein the circular opening and the slot opening are interconnected to form one opening that is enclosed by the configurable guide insert.

9. The cannula of claim 8, wherein the opening into the bore between axially-extending edges of the sidewall is enclosed by the base member.

10. The cannula of claim 1, further comprising a support surface at the distal end configured to support soft tissue of the patient wherein the support surface is flat and extends in a direction perpendicular to the axial direction.

11. The cannula of claim 1, further comprising:

an obturator, wherein the combination track is configured to slidably receive the obturator through the circular opening and into the bore when the configurable guide insert is positioned in the right orientation for the surgical procedure in the right side of the patient or in the left orientation for the surgical procedure in the left side of the patient.

12. The cannula of claim 11, further comprising the obturator slidably insertable into the cannula for at least partially covering the opening during insertion of the cannula into a patient incision, wherein the obturator includes a set of markings configured to indicate whether the obturator is positioned within the circular opening in the right orientation for the surgical procedure in the right side of the patient or in the left orientation for the surgical procedure in the left side of the patient.

13. A surgical device comprising:

a cannula; and a configurable guide insert coupled to the cannula, the configurable guide insert having a combination track including:

a circular opening configured to receive a first surgical implement, and a slot opening configured to receive a second surgical implement, each of the circular opening and the slot opening extending through the configurable guide insert; and a set of markings on the configurable guide insert;

wherein the configurable guide insert may be positioned in a configurable orientation comprising a right orientation for a surgical procedure in a right side of a patient or a left orientation for the surgical procedure in a left side of the patient;

wherein the set of markings indicates whether the configurable guide insert is positioned in the right orientation or in the left orientation, and wherein the configurable guide insert is configured for rotation of 180 degrees about an axis defined in relation to the cannula when positioning the configurable guide insert relative to the cannula from the right orientation to the left orientation or from the left orientation to the right orientation.

14. The surgical device of claim 13, wherein the second surgical implement includes an acting feature and a sliding feature; and the cannula comprises:

a base member at a proximal end;

a sidewall connected to the base member and extending in an axial direction from the proximal end to a distal end; and a bore extending in the axial direction defined by the base member and the sidewall, the sidewall further defining an opening into the bore between axially-extending edges of the sidewall;

wherein the configurable guide insert is disposed on the base member and the circular opening providing passage to the base member into the bore and the slot opening providing passage to the base member into an action area outside the opening of the bore and radially between the edges of the sidewall;

wherein the combination track slidably receives the first surgical implement through the circular opening and into the bore and slidably receives the second surgical implement through the slot opening and into the action area via the sliding feature; and wherein the configurable guide insert is positionable in the right orientation for positioning of the first and second surgical implements for a surgical procedure in the right side of the patient, or in the left orientation for positioning of the first and second surgical implements for the surgical procedure in the left side of the patient.

15. The surgical device of claim 13, wherein the axis defined in relation to the cannula is parallel or equal to a longitudinal axis defined by the cannula.

16. The surgical device of claim 15, wherein the configurable guide insert further comprises a push button configured to rotate the configurable guide insert for rotation of 180 degrees about an axis perpendicular to the longitudinal axis defined by the cannula when positioning the configurable guide insert relative to the cannula from the right orientation to the left orientation or from the left orientation to the right orientation.

17. The surgical device of claim 13, wherein the axis defined in relation to the cannula is perpendicular to a longitudinal axis defined by the cannula.

18. The surgical device of claim 17, wherein the configurable guide insert further comprises a push button configured to rotate the configurable guide insert for rotation of 180 degrees about an axis parallel to the longitudinal axis defined by the cannula when positioning the configurable guide insert relative to the cannula from the right orientation to the left orientation or from the left orientation to the right orientation.

19. The surgical device of claim 13, wherein the configurable guide insert is rigidly locked into the configurable orientation.

20. A method of performing a surgical procedure, comprising:

providing a cannula, the cannula including a base member and a configurable guide insert coupled to the base member;

providing a removable obturator configured to slidably insert within the cannula through the configurable guide insert and base member;

wherein the configurable guide insert includes a marking to indicate whether the configurable guide insert is positioned in a right orientation or in a left orientation, and wherein the comprising configurable guide insert defines a combination track, the combination track further comprising:

a circular opening extending through the configurable guide insert and into a bore within the cannula formed by a sidewall of the cannula; and a slot opening extending through the configurable guide insert and into an action area outside of the bore and radially between axially-extending edges of the sidewall;

determining whether the configurable guide insert will be positioned in the right orientation for a surgical procedure in a right side of a patient or in the left orientation for the surgical procedure in a left side of the patient;

wherein the configurable guide insert is configured for rotation of 180 degrees about an axis defined in relation to the cannula when positioning the configurable guide insert on the base member in the right orientation or in the left orientation;

rotating the configurable guide insert within the base member in either the right orientation for the surgical procedure in the right side of the patient or in the left orientation for the surgical procedure in the left side of the patient;

inserting the obturator into the bore through the circular opening of the combination track and sliding the obturator toward a distal end of the cannula;

inserting the cannula into an incision in either the left side of the patient or the right side of the patient;

removing the obturator from the cannula while leaving the cannula in place within the incision in either the left side of the patient or the right side of the patient;

inserting a camera device into the bore through the circular opening of the combination track and sliding the camera device toward the distal end of the cannula;

providing an image of a target tissue via the camera device;

inserting a tissue manipulation device through the slot opening of the combination track and sliding the tissue manipulation device toward the distal end of the cannula and into the action area; and manipulating the target tissue via the tissue manipulation device.

* * * * *